United States Patent [19]
King

[11] Patent Number: 5,214,142
[45] Date of Patent: May 25, 1993

[54] PROCESSES FOR THE PREPARATION OF AMINOETHERS

[75] Inventor: Stephen W. King, Scott Depot, W. Va.

[73] Assignee: Union Carbide Chemicals & Plastics Technology Corporation, Danbury, Conn.

[21] Appl. No.: 585,563

[22] Filed: Sep. 20, 1990

[51] Int. Cl.$^5$ .................. C07D 413/12; C07C 209/68
[52] U.S. Cl. .................... 544/111; 544/177; 544/401; 564/467; 564/503; 564/506; 564/508; 564/511
[58] Field of Search ............... 544/111, 177, 401; 564/467, 508, 503, 506, 511

[56] References Cited

U.S. PATENT DOCUMENTS

| | | | |
|---|---|---|---|
| 2,691,017 | 10/1954 | Bornfeld | 260/247.2 |
| 3,082,598 | 3/1963 | Mahan | 60/35.4 |
| 3,330,782 | 7/1967 | Poppelsdorf | 260/2.5 |
| 3,400,157 | 9/1968 | Poppelsdorf | 260/584 |
| 3,426,072 | 2/1969 | Warner | 260/584 |
| 3,480,675 | 11/1969 | Poppelsdorf | 260/584 |
| 3,957,875 | 5/1976 | Ferrell et al. | 260/585 B |
| 4,177,212 | 12/1979 | Poppelsdorf | 260/584 R |
| 4,247,482 | 1/1981 | Poppelsdorf | 564/508 |
| 4,374,259 | 2/1983 | McEntire | 549/518 |

FOREIGN PATENT DOCUMENTS

| | | |
|---|---|---|
| 2824908 | 12/1979 | Denmark . |
| 0115071 | 8/1984 | European Pat. Off. . |
| 0297296 | 1/1989 | European Pat. Off. . |
| 0300323 | 1/1989 | European Pat. Off. . |
| 1290148 | 3/1969 | Fed. Rep. of Germany . |
| 3422610 | 12/1985 | Fed. Rep. of Germany . |

OTHER PUBLICATIONS

March, J., Advanced Organic Chemistry: Reactions, Mechanisms, and Structure, 1968, pp. 435–436, 477–480 and 878–879.
Tamura, Y. et al., Synthesis, 1975, pp. 641–642.
Enichem Synthesis SpA, Dimethyl Carbonate Product Bulletin p. 10, (1980).
Taylor, Roger, Tetrahedron Letters, No. 8, 1975, pp. 593–596.
Witt, H. et al., Angew. Chem., 1970, 82, p. 79.
Tundo, Pietro et al., Ind. Eng. Chem. Res., 1988, 27, pp. 1565–1571.
Chemical Abstracts, vol. 109, No. 1, Jul. 4, 1988 Pierre Braunstein et al. "Synthesis of anisole by Lewis acid catalysed decarboxylation of methyl phenyl carbonate." abstract-No. 6 156w.
Chemical Abstracts, vol. 108, No. 14, Apr. 4, 1988, Yoshiyuki Harano "Manufacture of alkyl phenyl ethers," abstract-No. 144 679g.
Chemical Abstracts, vol. 98, No. 22, May 30, 1982, Rudi Van Eldik et al. "Mechanistic information on the acid-catalyzed decarboxylation of carbonatobis-(ethylenediamine) cobalt (III) ion in aqueous solution using rapid scan spectrophotometry" abstract-No. 186 385f.
Chemical Abstracts, vol. 83, No. 5, Aug. 4, 1975 Roger Taylor "Thermal decomposition of carbonates to ethers," abstract-No. 42 402b.
Chemical Abstracts, vol. 62, No. 1, Jan. 4, 1965, Klara Dora "Some pentamethonium isoteric derivatives." abstract No 439c.
Chemical Abstracts, vol. 52, No. 13, Jul. 10, 1958, Jorgen Fakstorp et al. "Bifunctional amines and ammonium compounds, VI, Further homologs and analogs of bis-choline ether salts." abstract-No. 10 876g.
Chemical Abstracts, vol. 53, No. 12, Jun. 25, 1959. Aktiebolaget Pharmacia "Bis(quaternary ammonium-alkyl) ethers." abstract-No. 11 230a, 1980.
Chemical Abstracts, vol. 62, No. 6, Mar. 15, 1965 Frisco G. Willeboordse et al. "Kinetics and catalysis of urethan foam reactions." abstract-No. 6 624h.
Chemical Abstracts, vol. 69, No. 7, Aug. 12, 1968 Robert B. Angier et al. "Antiviral agents, I. Analogs and derivatives of 2-diethyl-aminoethyl 4-methyl-piperazine-1-carboxylate." abstract-No. 27 378r.

Primary Examiner—Johann Richter
Attorney, Agent, or Firm—R. M. Allen

[57] ABSTRACT

A process for preparing aminoethers, particularly bis[2-(N,N-dialkylamino)alkyl]ethers, which comprises contacting a carboxylated aminoether with a metal oxide catalyst under conditions effective to produce the aminoether. Many of these aminoethers are useful as catalysts in the production of polyurethanes, especially cellular polyurethanes.

56 Claims, No Drawings

PROCESSES FOR THE PREPARATION OF AMINOETHERS

RELATED APPLICATIONS

The following are related, commonly assigned applications, filed on an even date herewith:

U.S. patent application Ser. No. 07/585,455; U.S. patent application Ser. No. 07/585,559; U.S. patent application Ser. No. 07/585,456; U.S. patent application Ser. No. 07/585,565; U.S. patent application Ser. No. 07/585,555 now U.S. Pat. No. 5,104,987; and U.S. patent application Ser. No. 07/585,556 now U.S. Pat. No. 5,164,497; all of which are incorporated herein by reference.

BRIEF SUMMARY OF THE INVENTION

1. Technical Field p This invention relates to a process for preparing aminoethers, particularly bis[2-(N,N-dialkylamino)alkyl]ethers, which comprises contacting a carboxylated aminoether with a metal oxide catalyst under conditions effective to produce the aminoether. Many of these aminoethers are useful as catalysts in the production of polyurethanes, especially cellular polyurethanes.

2. Background of the Invention

Decarboxylation, that is, elimination of the —COOH group as $CO_2$, is a known process. March, J., Advanced Organic Chemistry: Reactions, Mechanisms, and Structure, 1968, pp. 435–436, 477–480 and 878–879, describes various decarboxylation reactions. At pages 435–436, it is stated that aromatic acids can be decarboxylated by heating with copper and quinoline. At pages 477–480, it is stated that aliphatic acids which undergo successful decarboxylation have certain functional groups or double or triple bonds in the alpha or beta positions such as malonic acids, alpha-cyano acids, alpha-nitro acids, alpha-aryl acids, alpha-keto acids, alpha-trihalo acids, beta-keto acids, beta,gamma-olefinic acids and the like. At pages 878–879, oxidative decarboxylation is described in which lead tetraacetate cleaves carboxyl groups, replacing them with acetoxy groups, which may be hydrolyzed to hydroxyl groups. It is stated that compounds containing carboxyl groups on adjacent carbons (succinic acid derivatives) can be bisdecarboxylated with lead tetraacetate. It is also stated that compounds containing geminal carboxyl groups (malonic acid derivatives) can be bisdecarboxylated with lead tetraacetate, gem-diacetates (acylals) being produced, which are hydrolyzable to ketones.

Tamura, Y. et al., Synthesis, 1975, 641–642, relates to the preparation of unsymmetrical sulfides by the alkylation of thiols with alkyl carbonates in the presence of sodium ethoxide and ethanol under refluxing conditions.

Enichem Synthesis SpA, Dimethyl Carbonate Product Bulletin, p. 10, discloses the reaction of phenols with dimethyl carbonate in the presence of a basic catalyst such as NaOH, $Na_2CO_3$, $NaOCH_3$, tertiary amines or heterocyclic nitrogenous compounds to give methylated phenols. Reaction temperatures of at least 140° C. are required. It is stated that the speed of reaction can be accelerated with catalytic quantities of organic and inorganic halides.

Taylor, Roger, Tetrahedron Letters, No. 8, 1975, 593–596, discloses the thermal decomposition of carbonates to ethers utilizing a palladium-charcoal catalyst.

Witt, H. et al., Angew. Chem., 1970, 82, 79, describes the preparation of substituted diphenyl ethers from ortho- and para-substituted diphenyl carbonates in the presence of small amounts of potassium carbonate and at a temperature of 180° C.–260° C.

Tundo, Pietro et al., Ind. Eng. Chem. Res., 1988, 27, 1565–1571, describes the reaction of dialkyl carbonates with phenols, thiophenols and mercaptans under gas-liquid phase-transfer conditions (continuous flow of gaseous reactants over a solid bed supporting a liquid phase-transfer catalyst) to produce the corresponding ethers and thioethers. The solid bed consisted of potassium carbonate coated with 5 weight percent of CARBOWAX® poly(oxyethylene)glycol 6000 for one set of experiments and alpha-alumina pellets coated with 5 weight percent of potassium carbonate and 5 weight percent of CARBOWAX® poly(oxyethylene)glycol 6000 for another set of experiments. Tundo et al. state at page 1568, right hand column, lines 33–42, that the reaction of alcohols with dialkyl carbonates produces only transesterification.

Bis[beta-(N,N-dimethylamino)alkyl]ethers, such as bis[2-(N,N-dimethylamino)ethyl]ether, are known to be valuable polyurethane catalysts, particularly in the production of flexible polyurethane foam. The production of polyurethane foam by reacting an organic isocyanate with an active hydrogen-containing compound (polyol) in the presence of a bis[beta-(N,N-dimethylamino)alkyl]ether catalyst is disclosed in U.S. Pat. No. 3,330,782.

Several processes for the production of bis[beta-(N,N-dimethylamino)alkyl]ethers, including bis[2-(N,N-dimethylamino)ethyl]ether, are known. U.S. Pat. No. 3,400,157 discloses the production of bis[beta-(N,N-dimethylamino)alkyl]ethers from bis(beta-haloalkyl)ethers, e.g., bis(2-chloroethyl)ether, by reaction with trimethylamine to form the bis-methohalide of bis[beta-(N,N-dimethylamino)alkyl]ether and subsequently reacting the latter compound with dimethylamine to form the desired ether product. U.S. Pat. No. 3,426,072 describes the production of bis[beta-(N,N-dimethylamino)alkyl]ethers by reaction of the bis-methohalide of bis[beta-(N,N-dimethylamino)alkyl]ether with a primary amine to form the desired ether product. However, there are disadvantages associated with the use of bis(2-chloroethyl)ether including the need to employ comparatively expensive corrosion resistant equipment because of the presence of chlorides in the reaction mixture and disposal problems associated with by-product chlorides.

Another process for the production of bis[beta-(N,N-dimethylamino)alkyl]ethers involves reacting a beta-(N,N-dimethylamino)alkanol with a beta-(N,N-dimethylamino)alkyl chloride (or acid salt thereof) in the presence of an alkali metal hydroxide using a modified Williamson ether synthesis as disclosed in U.S. Pat. No. 3,480,675. However, this modified Williamson synthesis has disadvantages including several solids handling steps, a discontinuous mode of operation, disposal problems associated with by-product sodium chloride, and one of the reactants, 2-dimethylaminoethyl chloride which is used in the production of bis[2-(N,N-dimethylamino)ethyl]ether, is an unstable liquid and is also a vesicant which requires special handling.

U.S. Pat. No. 3,957,875 discloses a process for the production of bis[2-(N,N-dimethylamino)ethyl]ether by reacting trimethylamine with bis[2-(N,N-dimethylamino)ethoxyl]ethanol in the presence of a nickel catalyst. However, this process requires the use of a costly high-pressure reactor and provides product yields that leave room for improvement.

U.S. Pat. No. 4,177,212 describes a process for producing bis[2-(N,N-dialkylamino)alkyl]ethers of the formula $(R_2NR')_2O$, wherein R is a methyl or ethyl group and R' is a bivalent alkylene group having from 2 to 3 carbon atoms. This process is effected by a two-step, "one pot" reaction that utilizes a chloro-containing compound selected from sulfuryl chloride, thionyl chloride and chlorosulfonic acid together with $R_2NR'ONa$ as reactants, wherein R and R' are as defined above. However, this process has disadvantages including disposal problems associated with the by-product sodium chloride and special handling required for the chloro-containing compounds.

U.S. Pat. No. 4,247,482 discloses a process for producing bis[2-(N,N-dialkylamino)alkyl]ethers of the formula $(R_2NR')_2O$, wherein R is a methyl or ethyl group and R' is a bivalent alkylene group having from 2 to 3 carbon atoms. This process is effected by a two-step, preferably "one pot", reaction that utilizes $SO_3$ vapor and $R_2NR'ONa$ as reactants, wherein R and R' are defined above. However, this process has disadvantages including disposal problems associated with the by-product sodium sulfate and the need to employ comparatively expensive corrosion resistant equipment because of the presence of $SO_3$ vapor in the reaction mixture.

U.S. Pat. No. 2,691,017 describes a process for the production of bis-aminoalkyl carbonate derivatives. Example 1 thereof demonstrates the preparation of bis[2-(N,N-dimethylamino)ethyl]carbonate by reacting diethyl carbonate and 2-(N,N-dimethylamino)ethanol in the presence of potassium carbonate at elevated temperature.

Accordingly, it is desirable to provide processes for the production of aminoethers, particularly bis[2-(N,N-dialkylamino)alkyl]ethers, including bis[2-(N,N-dimethylamino)ethyl]ether, that do not possess the disadvantages associated with the above-mentioned processes.

DISCLOSURE OF THE INVENTION

This invention relates to a process for preparing aminoethers which comprises contacting a carboxylated aminoether with a metal oxide catalyst under conditions effective to produce the aminoether.

This invention also relates to a process for preparing aminoethers which comprises contacting an active hydrogen-containing compound with a $CO_2$ synthon in the presence of a metal oxide catalyst under conditions effective to produce the aminoether, provided at least one of the active hydrogen-containing compound and $CO_2$ synthon contains nitrogen.

This invention further relates to a process for preparing aminoethers which comprises (i) contacting an active hydrogen-containing compound with a $CO_2$ synthon under conditions effective to produce a carboxylated aminoether, and (ii) contacting the carboxylated aminoether with a metal oxide catalyst under conditions effective to produce the aminoether, provided at least one of the active hydrogen-containing compound and $CO_2$ synthon contains nitrogen.

This invention yet further relates to a process for preparing bis[2-(N,N-dialkylamino)-alkyl]ethers which comprises contacting a bis[2-(N,N-dialkylamino)alkyl]carbonate with a metal oxide catalyst under conditions effective to produce the bis[2-(N,N-dialkylamino)alkyl]ether.

This invention relates also to a process for preparing bis[2-(N,N-dialkylamino)alkyl]ethers which comprises contacting a 2-(N,N-dialkylamino)-alkanol with a dialkyl carbonate in the presence of a metal oxide catalyst under conditions effective to produce the bis[2-(N,N-dialkylamino)alkyl]ether.

This invention relates further to a process for preparing bis[2-(N,N-dialkylamino)alkyl]ethers which comprises (i) contacting a 2-(N,N-dialkylamino)alkanol with a dialkyl carbonate under conditions effective to produce a bis[2-(N,N-dialkylamino)alkyl]carbonate, and (ii) contacting the bis[2-(N,N-dialkylamino)alkyl]carbonate with a metal oxide catalyst under conditions effective to produce the bis[2-(N,N-dialkylamino)alkyl]ether.

Many of the aminoethers, particularly the bis[2-(N,N-dialkylamino)alkyl]ethers, produced in accordance with the processes of this invention are useful for a variety of applications such as catalysts in the production of cellular polyurethanes. One such catalyst, bis[2-(N,N-dimethylamino)ethyl]ether, is particularly useful in the production of flexible polyurethane foam. Other applications include, for example, acid gas scrubbing agents, agricultural formulations, pharmaceutical formulations, complexing agents and the like.

For purposes of this invention, the chemical elements are identified in accordance with the Periodic Table of the Elements, CAS version, Handbook of Chemistry and Physics, 67th Ed., 1986–87, inside cover. Also, for purposes of this invention, Group IIIB metal oxides embraces the lanthanides and actinides. As used herein, the term "oxide" embraces oxides, hydroxides and/or mixtures thereof. Also, as used herein, the term "$CO_2$ synthon" embraces $SO_2$ synthons such as sulfurous acids and sulfurous acid esters. Sulfur analogs of aminoethers, i.e., aminothioethers, are also embraced by this invention.

DETAILED DESCRIPTION

As indicated above, this invention relates to a process for preparing aminoethers which comprises contacting a carboxylated aminoether with a metal oxide catalyst under conditions effective to produce the aminoether.

As also indicated above, this invention relates to a process for preparing aminoethers which comprises contacting an active hydrogen-containing compound with a $CO_2$ synthon in the presence of a metal oxide catalyst under conditions effective to produce the aminoether, provided at least one of the active hydrogen-containing compound and $CO_2$ synthon contains nitrogen.

As further indicated above, this invention relates to a process for preparing aminoethers which comprises (i) contacting an active hydrogen-containing compound with a $CO_2$ synthon under conditions effective to produce a carboxylated aminoether, and (ii) contacting the carboxylated aminoether with a metal oxide catalyst under conditions effective to produce the aminoether, provided at least one of the active hydrogen-containing compound and $CO_2$ synthon contains nitrogen.

As yet further indicated above, this invention relates to a process for preparing bis[2-(N,N-dialkylamino)alkyl]ethers which comprises contacting a bis[2-(N,N-dialkylamino)alkyl]carbonate with a metal oxide catalyst under conditions effective to produce the bis[2-(N,N-dialkylamino)alkyl]ether.

As indicated also above, this invention relates to a process for preparing bis[2-(N,N-dialkylamino)alkyl]ethers which comprises contacting a 2-[N,N-dialkylamino)alkanol with a dialkyl carbonate in the presence of a metal oxide catalyst under conditions effective to produce the bis[2-(N,N-dialkylamino)alkyl]ether.

As indicated further above, this invention relates to a process for preparing bis[2-(N,N-dialkylamino)alkyl]ethers which comprises (i) contacting a 2-(N,N-dialkylamino)alkanol with a dialkyl carbonate under conditions effective to produce a bis[2-(N,N-dialkylamino)alkyl]carbonate, and (ii) contacting the bis[2-(N,N-dialkylamino)alkyl]carbonate with a metal oxide catalyst under conditions effective to produce the bis[2-(N,N-dialkylamino)alkyl]ether.

In a preferred embodiment, this invention relates to a process for preparing bis[2-(N,N-dimethylamino)ethyl]ether which comprises contacting bis[2-(N,N-dimethylamino)ethyl]carbonate with a magnesium:aluminum mixed metal oxide catalyst under conditions effective to produce bis[2-(N,N-dimethylamino)ethyl]ether.

In another preferred embodiment, this invention relates to a process for preparing bis[2-(N,N-dimethylamino)ethyl]ether which comprises contacting 2-(N,N-dimethylamino)ethanol with diethyl carbonate in the presence of a magnesium:aluminum mixed metal oxide catalyst under conditions effective to produce bis[2-(N,N-dimethylamino)ethyl]ether.

In a further preferred embodiment, this invention relates to a process for preparing bis[2-(N,N-dimethylamino)ethyl]ether which comprises (i) contacting 2-(N,N-dimethylamino)ethanol with diethyl carbonate under conditions effective to produce bis[2-(N,N-dimethylamino)ethyl]carbonate, and (ii) contacting bis[2-(N,N-dimethylamino)ethyl]carbonate with a magnesium:aluminum mixed metal oxide catalyst under conditions effective to produce bis[2-(N,N-dimethylamino)ethyl]ether.

When an active hydrogen-containing compound and $CO_2$ synthon are employed as starting materials, it is believed that a transesterification reaction followed by a decarboxylation reaction occurs to provide the desired aminoether product. The exact reaction mechanism is not fully appreciated but what is appreciated is that an active hydrogen-containing compound starting material and $CO_2$ synthon starting material can be contacted in the presence of a metal oxide catalyst under conditions described herein to provide an aminoether product. It is also appreciated that a carboxylated aminoether can be contacted with a metal oxide catalyst under conditions described herein to provide an aminoether product.

Step (i) of certain processes of this invention can in general be referred to as a transesterification reaction. Any suitable transesterification catalyst can be employed in step (i). Such transesterification catalysts are known and include, for example, basic metal oxides, alkoxides and other basic metal salts such as potassium carbonate, sodium 2-dimethylaminoethoxide and the like. Other suitable transesterification catalysts include, for example, Bronsted acids such as sulfuric acid and Lewis acids such as aluminum triisopropoxide. As discussed hereinafter in regard to the decarboxylation catalyst, the transesterification catalyst employed in this invention likewise may also contain support(s), binding agent(s) or other additives to stabilize or otherwise help in the manufacture of the catalyst. Both homogeneous and heterogeneous catalysts can be employed in the step (i) reaction. The amount of transesterification catalyst used in step (i) is dependent on the particular catalyst employed and can range from about 0.01 weight percent or less to about 10 weight percent or greater of the total weight of the starting materials.

Suitable active hydrogen-containing compound starting materials which can be employed in the step (i) transesterification reaction include any permissible substituted or unsubstituted active hydrogen-containing organic compound(s). Illustrative active hydrogen-containing compound starting materials useful in this invention include, for example, substituted and unsubstituted alcohols, phenols, carboxylic acids, amines and the like. Preferred active hydrogen-containing compounds have at least one nitrogen atom. The molar ratio of active hydrogen-containing compound to $CO_2$ synthon is not narrowly critical and can range from about 0.05:1 or less to about 50:1 or greater, preferably from about 0.1:1 to about 10:1.

Suitable active hydrogen-containing compounds include substituted and unsubstituted alcohols (mono-, di- and polyhydric alcohols), phenols, carboxylic acids (mono-, di- and polyacids), and amines (primary and secondary). Other suitable active hydrogen-containing compounds include substituted and unsubstituted thiophenols, mercaptans, amides and the like. Frequently, the organic compounds contain 1 carbon to about 100 or 150 carbons (in the case of polyol polymers) and can contain aliphatic and/or aromatic structures. Most often, the organic compounds are selected from the group of mono-, di- and trihydric alcohols having 1 to about 30 carbon atoms. The organic compounds having active hydrogens can be the product of hydroformylation/hydrogenation reactions.

Suitable alcohols include primary and secondary monohydric alcohols which are straight or branched chain such as methanol, ethanol, propanol, pentanol, hexanol, heptanol, octanol, nonanol, decanol, undecanol, dodecanol, tridecanol, tetradecanol, pentadecanol, hexadecanol, octadecanol, isopropyl alcohol, 2-ethylhexanol, sec-butanol, isobutanol, 2-pentanol, 3-pentanol and isodecanol. Particularly suitable alcohols are linear and branched primary alcohols (including mixtures) such as produced by the "Oxo" reaction of $C_3$ to $C_{20}$ olefins. The alcohols may also be cycloaliphatic such as cyclopentanol, cyclohexanol, cycloheptanol, cyclooctanol, as well as aromatic substituted aliphatic alcohols such as benzyl alcohol, phenylethyl alcohol, and phenylpropyl alcohol. Other aliphatic structures include 2-methoxyethanol and the like.

Phenols include alkylphenols of up to 30 carbons such as p-methylphenol, p-ethylphenol, p-butylphenol, p-heptylphenol, p-nonylphenol, dinonylphenol and p-decylphenol. The aromatic radicals may contain other substituents such as halide atoms.

Alcohols (polyols) having 2 or more hydroxyl groups, e.g., about two to six hydroxyl groups and have 2 to 30 carbons, include glycols such as ethylene glycol, propylene glycol, butylene glycol, pentylene glycol, hexylene glycol, neopentylene glycol, decylene glycol, diethylene glycol, triethylene glycol and dipropylene glycol. Other polyols include glycerine, 1,3-propanediol, pentaerythritol, galactitol, sorbitol, mannitol, erythritol, trimethylolethane and trimethylolpropane.

Carboxylic acids include formic acid, acetic acid, propionic acid, butyric acid, valeric acid, caproic acid, caprylic acid, capric acid, lauric acid, myristic acid, palmitic acid, stearic acid, oleic acid, linoleic acid and linolenic acid. Other carboxylic acids include benzoic acid, cyclohexane carboxylic acid, phenylacetic acid, toluic acid, chlorobenzoic acid, bromobenzoic acid, nitrobenzoic acid, phthalic acid, isophthalic acid, terephthalic acid, salicylic acid, hydroxybenzoic acid, anthranilic acid, aminobenzoic acid, methoxybenzoic acid and the like.

Amines include methylamine, dimethylamine, ethylamine, diethylamine, n-propylamine, di-n-propylamine, isopropylamine, n-butylamine, isobutylamine, cyclohexylamine, piperazine, benzylamine, phenylethylamine, monoethanolamine, diethanolamine, aminoethylethanolamine, ethylenediamine, diethylenetriamine, triethylenetetramine, tetraethylenepentamine, pentaethylenehexamine, tetramethylenediamine and hexamethylenediamine. Other amines include aniline, methylaniline, toluidine, anisidine, chloroaniline, bromoaniline, nitroaniline, diphenylamines, phenylenediamine, benzidine, aminobenzoic acid, sulfanilic acid and sulfanilamide. Still other amines include acetanilide, benzanilide, aceto-toluidide, nitroacetanilide and the like.

Preferred active hydrogen-containing starting materials which can be employed in the step (i) transesterification reaction include alkanolamines such as those embraced by the formula ROH wherein R is the residue of an organic compound containing nitrogen. Preferred alkanolamine starting materials include 2-(N,N-dialkylamino)alkanols such as those embraced by the formula $R_1R_2NR_3OH$ wherein $R_1$ is a methyl or ethyl group, $R_2$ is a methyl or ethyl group, and $R_3$ is a bivalent alkylene group having from 2 to 4 carbon atoms.

Illustrative of preferred active hydrogen-containing starting materials useful in this invention include, for example, 2-(N,N-dimethylamino)ethanol, 2-(N,N-diethylamino)ethanol, 1-(N,N-dimethylamino)-2-propanol, 4-(2-hydroxyethyl)piperazine, morpholine, 4-(2-hydroxyethyl)morpholine, diethylene glycol, N,N-dimethylaminoethoxyethanol, bis(2-aminoethyl)ether and the like.

Suitable $CO_2$ synthon starting materials which can be employed in the step (i) transesterification reaction include any permissible substituted or unsubstituted carboxyl-containing compound(s) or carbonyl-containing compound(s) which are capable of reacting with an active hydrogen-containing compound under the process conditions described herein, such as those embraced by the formulae $R_4C(O)R_5$ or $R_4S(O)R_5$ wherein $R_4$ is hydrogen, halogen, amino, hydroxyl or the residue of an organic compound, and $R_5$ is amino, hydroxyl or the residue of an organic compound. Illustrative $CO_2$ synthons include, for example, substituted and unsubstituted carbonates, chlorocarbonates, carbonic acids, carbamates, carbamic acids, oxalates, 2-oxazolidinones, ureas, esters, phosgene, chloroformates, carbon dioxide, orthocarboxylates, sulfurous acids, sulfurous acid esters and the like. For purposes of this invention, carbon monoxide is also considered a $CO_2$ synthon for appropriate oxidative carbonylation reactions. Preferred $CO_2$ synthons include, for example, diethyl carbonate, ethylene carbonate, dimethyl carbonate, 2-oxazolidinone, ethylene sulfite, urea, phosgene, N,N,N',N'-tetramethyl urea and the like. The use of $CO_2$ synthons prepared in situ such as the reaction of ethylene carbonate and monoethanolamine to give 2-oxazolidinone is encompassed within the scope of this invention.

As indicated above, $R_4$ and $R_5$ can be the residue of an organic compound. Illustrative residues of organic compounds include, for example, alkyl, aryl, alkylamino, arylamino, cycloalkyl, heterocycloalkyl, alkyloxy, aryloxy, cycloalkyloxy, heterocycloalkyloxy, alkyloxycarbonyl, aryloxycarbonyl, cycloalkyloxycarbonyl, heterocycloalkyloxycarbonyl, hydroxycarbonyl and the like. Additionally, for purposes of defining the $CO_2$ synthon by the formulae above, the $R_4$ and $R_5$ substituents together can complete a cycloalkyl ring or a heterocycloalkyl ring which can be substituted or unsubstituted. The $R_4C(O)R_5$ formula is also contemplated to embrace carbon dioxide and carbon monoxide.

The step (i) transesterification reaction can be conducted over a wide range of pressures ranging from atmospheric or subatmospheric pressures to superatmospheric pressures. However, the use of very high pressures has not been observed to confer any significant advantages but increases equipment costs. Further, it is preferable to conduct the step (i) reaction at reduced pressures of from about 1 mm Hg to less than about 760 mm Hg. The step (i) transesterification reaction is preferably effected in the liquid or vapor states or mixtures thereof.

The temperature of the step (i) transesterification reaction may be as low as about ambient temperature to about 300° C. Preferably, the reaction temperature ranges from about 40° C. to about 200° C., and most preferably from about 60° C. to about 150° C.

Suitable carboxylated aminoethers prepared by the step (i) transesterification reaction include any permissible substituted or unsubstituted carboxyl-containing aminoether compounds which are capable of eliminating carbon dioxide under the process conditions described herein, e.g., esters, carbonates, carbamates and the like, such as those embraced by the formulae ROC(O)OR$_4$, ROC(O)OR$_5$, ROC(O)OC(O)OR$_4$, ROC(O)OC(O)OR$_5$ and the like wherein R, $R_4$ and $R_5$ are as defined above. It is understood that the R and $R_4$ substituents together and the R and $R_5$ substituents together can complete a heterocycloalkyl ring which can be substituted or unsubstituted. Preferred carboxylated aminoethers include bis[2-(N,N-dialkylamino)alkyl]carbonates such as those embraced by the formula $R_1R_2NR_3OC(O)OR_3NR_2R_1$ wherein $R_1$, $R_2$ and $R_3$ are as defined above. Other preferred carboxylated aminoethers prepared by the step (i) transesterification reaction include those embraced by the formulae $R_1R_2NR_3OC(O)OR_4$ or $R_1R_2NR_3OC(O)OR_5$ wherein $R_1$, $R_2$, $R_3$, $R_4$ and $R_5$ are as defined above. Illustrative carboxylated aminoethers useful in this invention include, for example, bis[2-(N,N-dimethylamino)ethyl]carbonate, bis[2-(N,N-dimethylamino)-1-methylethyl]carbonate, bis[2-(N,N-dimethylamino)propyl]carbonate, bis[3-(N,N-dimethylamino)propyl]carbonate, bis[2-(N,N-diethylamino)ethyl]carbonate, bis[2-(N,N-diethylamino)-1-methylethyl]carbonate, bis[2-(N,N-diethylamino)propyl]carbonate, bis(2-N-morpholinoethyl)carbonate, 2-(N,N-dimethylamino)ethyl ethyl carbonate, [2-(2'-dimethylamino)ethyl] N,N-dimethyl carbonate, 4-(2-hydroxyethyl)morpholine methyl carbonate, (2-dimethylaminoethyl-3-dimethylaminopropyl)carbonate and the like. The preferred bis[2-(N,N-dialkylamino)alkyl]carbonate is bis[2-(N,N-dimethylamino)ethyl]carbonate. U.S. Pat. No. 2,691,017, the disclosure of which is incorporated herein by reference, discloses bis[2-(N,N-dialkylamino)alkyl]carbonates which can be employed in step (ii) of certain processes of this invention. The amount of carboxylated aminoether(s) employed in step (ii) is dependent on the amount of metal oxide catalyst employed.

The carboxylated aminoethers prepared by the step (i) transesterification reaction may undergo one or more transesterifications prior to the step (ii) decarboxylation reaction. For example, an active hydrogen-containing compound different from the active hydrogen-containing compound starting material may be reacted with the originally prepared carboxylated aminoether under conditions effective to prepare a different carboxylated aminoether. Suitable active hydrogen-containing compounds include those embraced by the formula $R_6OH$ wherein $R_6$ is the residue of an organic compound containing nitrogen. This invention is not intended to be limited in any manner by the step (i) transesterification reaction.

The carboxylated aminoethers and aminoethers prepared in accordance with this invention can be either symmetrical or unsymmetrical. For the preparation of carboxylated aminoethers and aminoethers having a symmetrical configuration, it is preferred to use an alkylene carbonate, e.g., ethylene carbonate, as the $CO_2$ synthon starting material or a molar excess of any active hydrogen-containing compound starting material with any $CO_2$ synthon starting material, e.g., a molar ratio of active hydrogen-containing compound to $CO_2$ synthon of from about 3:1 to about 10:1. For the preparation of carboxylated aminoethers and aminoethers having an unsymmetrical configuration, it is Preferred to use a $CO_2$ synthon starting material other than an alkylene carbonate, e.g., dimethyl carbonate, or an equimolar or molar excess of any $CO_2$ synthon starting material with any active hydrogen-containing compound starting material, e.g., a molar ratio of active hydrogen-containing compound to $CO_2$ synthon of from about 0.1:1 to about 1:1.

Step (ii) of certain processes of this invention can in general be referred to as a decarboxylation reaction. Suitable decarboxylation catalysts which can be employed in step (ii) include one or more metal oxides. A magnesium:aluminum mixed metal oxide is a preferred metal oxide catalyst as more fully described below. Both homogeneous and heterogeneous catalysts can be employed in the step (ii) reaction. The amount of decarboxylation catalyst used in step (ii) is not narrowly critical and is dependent on whether step (ii) is conducted batchwise or continuously. If batchwise, the catalyst employed can range from about 0.01 weight percent or less to about 10 weight percent or greater of the total weight of the starting materials. If continuously, generally a fixed bed is employed.

Suitable decarboxylation catalysts for use in the processes of this invention comprise one or more metal oxides, preferably mixed metal oxides containing two or more metal oxides. Illustrative of such metal oxides include, for example, one or more of the following: Group IA metal oxides, Group IIA metal oxides, Group IIIB metal oxides (including lanthanides and actinides), Group IVB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides or Group VIA metal oxides. Certain of these metal oxides may also be used as transesterification catalysts in accordance with this invention such as Group IIA and IIIA metal oxides. Preferred metal oxides and mixed metal oxides are amphoteric or basic. Preferred metal oxides which may be utilized as decarboxylation catalysts include, for example, one or more oxides of magnesium, aluminum, calcium, strontium, gallium, beryllium, barium, scandium, yttrium, lanthanum, cerium, gadolinium, terbium, dysprosium, holmium, erbium, thulium, lutetium, ytterbium, niobium, tantalum, chromium, molybdenum, tungsten, titanium, zirconium, hafnium, vanadium, iron, cobalt, nickel, zinc, silver, cadmium, boron, indium, silicon, germanium, tin, lead, arsenic, antimony and bismuth.

Group IIA metal oxides such as magnesium oxide and calcium oxide and Group IIIA metal oxides such as aluminum oxide and gallium oxide are preferred mixed metal oxides for use in this invention. For mixed metal oxides in which at least one of the metals is magnesium, suitable metals in association with magnesium may include, for example, one or more of the following: Group IIIA metals such as boron, aluminum, gallium and indium, Group IIIB metals such as scandium, yttrium and lanthanum including the lanthanides, Group VB metals such as niobium and tantalum, Group VIB metals such as chromium, molybdenum and tungsten, Group VIII metals such as iron, cobalt and nickel, Group IIB metals such as zinc and cadmium, Group IVA metals such as silicon, germanium, tin and lead, Group VA metals such as arsenic, antimony and bismuth, and Group IVB metals such as zirconium and hafnium. For mixed metal oxides in which at least one of the metals is calcium, suitable metals in association with calcium may include, for example, one or more of the following: Group IIIA metals such as boron, aluminum, gallium and indium, Group IVA metals such as silicon, germanium, tin and lead, Group VB metals such as niobium and tantalum, and Group VIB metals such as chromium, molybdenum and tungsten.

Illustrative of mixed metal oxides which may be used as decarboxylation catalysts include, for example, $MgO-Al_2O_3$, $MgO-SiO_2$, $MgO-CdO$, $MgO-Bi_2O_3$, $MgO-Sb_2O_5$, $MgO-SnO_2$, $MgO-ZrO_2$, $MgO-BeO$, $MgO-TiO_2$, $MgO-CaO$, $MgO-SrO$, $MgO-ZnO$, $MgO-Ga_2O_3$, $MgO-Y_2O_3$, $MgO-La_2O_3$, $MgO-MoO_3$, $MgO-Mn_2O_3$, $MgO-Fe_2O_3$, $MgO-Co_3O_4$, $MgO-WO_3$, $MgO-V_2O_5$, $MgO-Cr_2O_3$, $MgO-ThO_2$, $MgO-Na_2O$, $MgO-BaO$, $MgO-CaO$, $MgO-HfO_2$, $MgO-Li_2O$, $MgO-Nb_2O_5$, $MgO-Ta_2O_5$, $MgO-Gd_2O_3$, $MgO-Lu_2O_3$, $MgO-Yb_2O_3$, $MgO-CeO_2$, $MgO-Sc_2O_3$, $MgO-PbO$, $MgO-NiO$, $MgO-CuO$, $MgO-CoO$, $MgO-B_2O_3$, $CaO-SiO_2$, $CaO-Al_2O_3$, $CaO-SnO$, $CaO-PbO$, $CaO-Nb_2O_5$, $CaO-Ta_2O_5$, $CaO-Cr_2O_3$, $CaO-MoO_3$, $CaO-WO_3$, $CaO-TiO_2$, $CaO-HfO_2$, $MgO-SiO_2-Al_2O_3$, $MgO-SiO_2-ZnO$, $MgO-SiO_2-ZrO_2$, $MgO-SiO_2-CuO$, $MgO-SiO_2-CaO$, $MgO-SiO_2-Fe_2O_3$, $MgO-SiO_2-B_2O_3$, $MgO-SiO_2-WO_3$, $MgO-SiO_2-Na_2O$, $MgO-SiO_2-Ga_2O_3$, $MgO-SiO_2-La_2O_3$, $MgO-SiO_2-Nb_2O_5$, $MgO-SiO_2-Mn_2O_3$, $MgO-SiO_2-Co_3O_4$, $MgO-SiO_2-NiO$, $MgO-SiO_2-PbO$, $MgO-SiO_2-Bi_2O_3$, $MgO-Al_2O_3-ZnO$ $MgO-Al_2O_3-Fe_2O_3$, $MgO-Al_2O_3-WO_3$, $MgO-Al_2O_3-ZrO_2$, $MgO-Al_2O_3-La_2O_3$, $MgO-Al_2O_3-Co_3O_4$, $CaO-SiO_2-Al_2O_3$, $CaO-SiO_2-Nb_2O_5$, $CaO-SiO_2-WO_3$, $CaO-SiO_2-SnO$, $CaO-SiO_2-TiO_2$, $CaO-SiO_2-MoO_3$, $CaO-SiO_2-HfO_2$, $CaO-SiO_2-Ta_2O_5$, $CaO-Al_2O_3-SiO_2$, $CaO-Al_2O_3-PbO$, $CaO-Al_2O_3-Nb_2O_5$, $CaO-Al_2O_3-WO_3$, $CaO-Al_2O_3-TiO_2$, $CaO-Al_2O_3-MoO_3$, $CaO-HfO_2-Al_2O_3$, $CaO-HfO_2-TiO_2$, and the like. Other suitable mixed metal oxides embraced within the scope of this invention are disclosed by Tanabe et al., Bulletin of the Chemical Society of Japan, Vol. 47(5), pp. 1064–1066 (1974).

The metal oxides described herein which can be used as decarboxylation catalysts may contribute to product selectivity and/or catalytic activity of the reaction and/or stability of the catalyst. As discussed hereinafter, the decarboxylation catalyst employed in this invention may also contain support(s), binding agent(s) or other additives to stabilize or otherwise help in the manufacture of the catalyst.

The decarboxylation catalysts which comprise one or more metal oxides may be prepared in a wide variety of ways. For example, the one or more metal oxides can be provided from metal salts which can either be heated or precipitated to form the metal oxides. Also, one or more metal oxides may be provided as a partial condensate on a support, such as a silica or alpha, beta or gamma alumina, silicon carbide, and the like, and then condensed by heating to effect polymerization to the desired oxide form. The one or more metal oxides may be condensed from hydrolyzable monomers to the desired oxide(s), indeed, to form oxide powders which can thereafter be compressed in the presence of a condensation catalyst to form pellets and larger structures of the metal oxide decarboxylation catalyst. A blend of the powders and condensation catalyst can be made into a shapeable paste which can be extruded and cut into pellets according to conventional procedures. The extrudate may thereafter be fired to cure the condensation catalyst and fix the structure. The cut extrudate may be blended with a support material such as those characterized above, and the blend fired to fuse the metal oxide catalyst to the support.

In a preferred embodiment of this invention, a magnesium salt, e.g., magnesium nitrate, and an aluminum salt, e.g., aluminum nitrate, are precipitated using ammonium hydroxide. The material is then washed with deionized water and calcined at a temperature of from about 350° C. to about 450° C. to afford the desired magnesium:aluminum mixed oxide catalyst.

In another preferred embodiment, a magnesium oxide, e.g., magnesium carbonate hydroxide pentahydrate, and an aluminum oxide, e.g., aluminum hydroxide hydrate, are added to deionized water and thoroughly mixed to from a paste. The paste is then calcined at a temperature of from about 350° C. to about 450° C. to afford the desired magnesium: aluminum mixed metal oxide catalyst.

A preferred catalyst structure comprises a Group IIA and IIIA mixed metal oxide having a surface area of at least about 100 m²/gm which may or may not be bonded to a support material. The decarboxylation catalysts on a support preferably H have a surface area greater than about 20 m²/gm to as high as about 260 m²/gm, or greater depending upon which metal oxides are employed. In the case of magnesium:aluminum oxides, the surface area can be greater than about 50 m²/gm to as high as about 260 m²/gm, more preferably, greater than about 100 m²/gm to as high as about 260 m²/gm, determined according to the single point $N_2$ method.

The term "support," as used herein and in the claims, means a solid structure which does not adversely affect the catalytic properties of the catalyst and is at least as stable as the catalyst to the reaction medium. The support can function as a decarboxylation catalyst independent of the metal oxide catalyst used herein, although it may have lower catalytic activity to the reaction. The support may act in concert with the catalyst to moderate the reaction. Some supports may contribute to the selectivity of the reaction. The catalyst structure can comprise from about 2 to about 60 percent by weight or greater of the support, more preferably from about 10 to about 50 percent by weight of the support, the remainder being the weight of the metal oxide(s). Included in the weight of the support is the weight of any binding agent such as phosphates, sulfates, silicates, fluorides, and the like, and any other additive provided to stabilize or otherwise help in the manufacture of the catalyst. The support may be particles as large or larger than the catalyst component and "glued" to the decarboxylation catalyst by virtue of a binding medium.

The support may constitute a separate phase in the process of extruding the catalytic structure. In this embodiment, the support forming material, preferably as a paste is blended with a paste of the decarboxylation catalyst or a partial condensate thereof. The paste may comprise the oxide forms of the support and the decarboxylation catalyst, each blended with water, and/or binding agents. The extrudate of the blend is passed through a multiorificed die and chopped into pellets of the desired sizes. The particles may be doughnut shaped, spherical, and the like. Then the particles are calcined to dry them and complete any condensation reaction in the support and/or the metal oxide decarboxylation catalyst.

A preferred group of mixed metal oxide catalysts for use in this invention include materials having the formula:

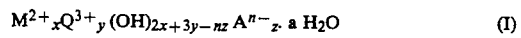

$$M^{2+}{}_x Q^{3+}{}_y (OH)_{2x+3y-nz} A^{n-}{}_z \cdot a\, H_2O \qquad (I)$$

wherein M is at least one divalent metal cation; Q is at least one trivalent metal cation; and A is at least one anion providing a valence (n−), wherein n is at least 1, e.g., between 1 and 4 and most often between 1 and 3, and wherein a is a positive number, M, Q, and A are provided in a proportion such that x/y is a number equal to or greater than 1, z has a value greater than zero and 2x+3y−nz is a positive number. M, Q and A may be selected to provide a layered structure. Preferably, x/y is in the range of 1 to 12, more preferably x/y is in the range of 1 to 6 and most preferably is in the range of 1 to 4. Preferably, z has a value such that x/z is between n and 12n, more preferably between n and 6n and most preferably between n and 4n.

Suitable divalent metal cations, M, broadly include elements selected from the Transition elements and Groups IIA and IVA of the Periodic Table as well as certain Group IIIB elements. As specific examples can be mentioned magnesium, calcium, titanium, vanadium, chromium, manganese, iron, cobalt, nickel, palladium, platinum, copper, zinc, cadmium, mercury, tin and lead. Divalent metal cations which are particularly suitable are magnesium, nickel, cobalt, zinc, calcium, strontium and copper. Suitable trivalent metal cations, Q, broadly include elements selected from the Transition elements and Groups IIIA and VA of the Periodic Table as well as certain Group IIIB elements. As specific examples can be mentioned aluminum, antimony, titanium, scandium, bismuth, vanadium, yttrium, chromium, iron, manganese, cobalt, ruthenium, nickel, gold, gallium, thallium, and cerium. Trivalent metal cations which are particularly suitable can be selected from aluminum, boron, gallium and lanthanum.

The composition of formula (I) also can include a wide range of anions, A. Any anion or combination of anions which can balance the charge of the cations can be used. Suitable anions include inter alia, halides (such as chloride, fluoride, bromide, and iodide), nitrite, nitrate, sulfite, sulfate, sulfonate, carbonate, chromate, cyanate, phosphite, phosphate, molybdocyanate, bicarbonate, hydroxide, arsenate, chlorate, ferrocyanide, borate, cyanide, cyanaurate, cyanaurite, ferricyanide, selenate, tellurate, bisulfate, as well as organic anions such as oxalate, acetate, hexanoate, sebacate, formate, benzoate, malonate, lactate, oleate, salicylate, stearate, citrate, tartrate, maleate, and the like. The class of metalate anions described in U.S. Pat. No. 4,667,045, including metavanadate, orthovanadate, molybdate, tungstate, hydrogen pyrovanadate and pyrovanadate, also are suitable as anion A. Anions suitable for use in combination with the metal cations previously identified as being particularly suitable are carbonate, halide, phosphate, chromate, sulfate, hydroxide, oxalate, acetate, nitrate, hexanoate, sebacate, vanadate, molybdate, tungstate and ferrocyanate.

The foregoing lists of suitable divalent and trivalent cations and suitable anions are meant to be illustrative and not exclusive. Those skilled in the art will recognize that other cations and anions can be used provided that the specific type of cations and their relative amounts (x/y ratio) and the specific type of anions and their relative amount result in a mixed metal oxide composition.

Included in the materials identified above are those based on exchangeable anionic clay minerals. For example, compositions of formula (I) wherein M is magnesium and Q is aluminum are related to hydrotalcites, while compositions in which M is nickel and A is aluminum are related to takovites. In fact, mixed metal oxides prepared using magnesium, nickel or cobalt as the divalent cation and aluminum as the trivalent cation exhibit the typical X-ray diffraction pattern of a hydrotalcite.

In a more preferred aspect, the processes of this invention can utilize mixed metal oxide catalyst compositions prepared by calcining at an elevated temperature compositions according to formula (I). Suitable calcined compositions have the general formula:

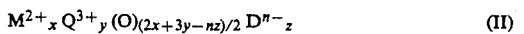

$$M^{2+}{}_x Q^{3+}{}_y (O)_{(2x+3y-nz)/2} D^{n-}{}_z \qquad (II)$$

wherein M, Q, x, y, z and n have the same meanings defined above in connection with formula (I), and D is at least one nonvolatile anion. Nonvolatile anions may include, inter alia, halides, nitrates, phosphites, phosphate, vanadate, molybdate, tungstate, sulfite, sulfate, chromate, arsenate, borate, chlorate and the like. This list is illustrative and not exclusive.

Heat treating the formula (I) compositions to prepare the calcined mixed metal oxide compositions of formula (II) can be done, for example, at a temperature in the range of 200° C. to 800° C. for a period of time of about 12 to 24 hours under an inert atmosphere such as nitrogen or in appropriate cases under an oxidizing atmosphere such as air.

Calcination of the mixed metal oxide composition dehydrates the composition and converts at least partially the metal hydroxides to metal oxides. Any nonvolatile anions may be present in the calcined material.

Provided the calcination temperature is not excessive, the mixed metal oxide can be rehydrated to the mixed metal hydroxide with water. Generally, the mixed metal oxide can be restored readily if the calcination temperature does not exceed about 600° C. Mixed metal oxides which are calcined under more severe conditions are not easily rehydrated and lower surface area materials are obtained.

Certain compositions falling within formula (I), such as hydrotalcite, which comprises a magnesium-aluminum hydroxide carbonate, and takovite, which comprises a nickel-aluminum hydroxide carbonate, are naturally occurring compositions. However, such compounds, as well as their related compositions, also can be prepared synthetically from inexpensive starting materials using well-known coprecipitation techniques. Procedures for direct synthesis of such materials are described in Itaya et al., *Inorg. Chem.* (1987) 26:624–626; Taylor, R. M., *Clay Minerals* (1984) 19: 591–603; Reichle, U.S. Pat. No. 4,476,324; Bish, D. L., *Bull. Mineral* (1980), 103:170–175 and Miyata et al., *Clays and Clay Minerals* (1977), 25:14–18. Using direct synthesis one has the ability to vary within wide limits the $M^{+2}/Q^{+3}$ atomic ratio as well as the anion.

For example, a composition of formula (I) where $M^{+2}$ is nickel or magnesium, $Q^{+3}$ is aluminum and $A^{n-}$ is carbonate can be prepared by adding, as aqueous solutions, (a) a mixture of nitrates, sulfates or chlorides of nickel or magnesium and aluminum in a desired atomic ratio of nickel or magnesium to aluminum, e.g. 6 atoms of nickel as nickel chloride to 2 atoms of aluminum as aluminum chloride, to (b) an aqueous solution of a stoichiometric amount of sodium hydroxide and a water soluble salt of the desired anion, e.g., sodium carbonate. The two solutions are mixed at a temperature of about 25° C. to 35° C. with vigorous stirring over a several-hour period to produce a slurry. The slurry then is heated for about 18 hours at a temperature within the range of about 50° C. to 200° C. (preferably between about 60° C. to 75° C.) in order to control crystallization and the ultimate particle size of the resulting crystals. After filtering, and thorough washing and drying, the solids are recovered, typically as a powder.

As noted above, this procedure can be adapted to a wide variety of cations, cation atomic ratios and anion substitutions. For example, water soluble salts of divalent magnesium, cobalt, zinc, copper, iron and calcium can be substituted for the nickel chloride illustrated above, while water soluble salts of trivalent gallium and lanthanum can replace the aluminum chloride. A wide variety of other combinations also will be apparent to those skilled in the art. Generally, the rate of metal ion addition to the aqueous caustic/anion solution is not critical and can be varied widely. For example, a preferred preparation method is described in Schaper, H. et al., *Applied Catalysis*, 54, 1989, 79–90, the disclosure of which is incorporated herein by reference. The reaction temperature also is not critical, although the temperature during the reaction preferably is kept below about 100° C. An important feature of the procedure is the use of efficient agitation during the mixing procedure to avoid the formation of undesired by-products.

Loading of an anion A or D into the mixed metal oxide compositions is influenced by a variety of factors including (i) the amount of anion used in the preparation relative to the metal cations, (ii) the atomic ratio of the metal cations (x/y) in the preparation procedure, (iii) the size of the cations and anions and (iv) the preparation procedure. As used herein, "loading" is defined as the amount of available valences provided by a desired anion A or D expressed as a percentage of the total available valences for anion A or D. For example, carbonate loading in a hydrotalcite-type catalyst can be maximized by (i) using an excess (e.g., a greater than 3:1 molar ratio) of sodium carbonate to aluminum chloride during catalyst preparation and (2) adjusting the atomic ratio of magnesium to aluminum cations to about 2:1.

Mixed metal oxide compositions suitable as catalysts also can be prepared from the native or synthetic hydrotalcite-type compositions by ion exchange. For example, hydrotalcite can be treated at ambient conditions with 0.01N phosphoric acid for about 18 hours to replace the carbonate anion with phosphate anion. A halide analog of hydrotalcite prepared directly or by anion-exchange could be contacted with molybdic acid or a water soluble salt thereof, or with a water soluble salt of tungstic acid or vanadic acid in order to substitute the transition metal anion for the halide anion in the catalyst structure thereby to produce a mixed metal oxide composition of formula (I). Other ion exchanges will be apparent to those skilled in the art.

Calcined mixed metal oxide compositions may exhibit a higher level of selectivity/activity than uncalcined compositions. If a calcined mixed metal oxide catalyst composition experiences any decline in selectivity, it can be regenerated by a heat treatment in the presence of air to restore at least a portion of its initial level of selectivity/activity enhancement and reused. Conditions discussed above for calcining the hydrated mixed metal oxide compositions are suitable for regenerating compositions which have experienced a decline in activity.

Catalysts having the formulas (I) and (II) above wherein M is at least one of magnesium and calcium, Q is aluminum or gallium, A is at least one of carbonate, bicarbonate, phosphate, sulfate and nitrate, x/y is between 1 and 20, z has a value which satisfies the relationship: x/z is between n and 12n, and a is a positive number, are generally preferred for vapor phase decarboxylation due to their combination of activity (conversion of precursor) and selectivity. A preferred process involves a vapor phase process using mixed metal oxide catalyst wherein $M^{2+}$ is magnesium, $Q^{3+}$ is aluminum, $A^{n-}$ is carbonate, x/y is about 1, and z is about 1.

The step (ii) decarboxylation reaction may be effected in the liquid or vapor or supercritical liquid states or mixtures thereof. In this context, the vapor phase reaction is intended to refer to the general vapor state of the starting materials. Though the step (ii) decarboxylation reaction conditions may range from subatmospheric or atmospheric to superatmospheric conditions, it is desirable to run the step (ii) reaction from about 1 mm Hg to about 5,000 mm Hg, preferably from about 100 mm Hg to about 2,500 mm Hg.

The temperature of the step (ii) decarboxylation reaction may be as low as about 150° C. to about 500° C. Preferably, the reaction temperature ranges from about 175° C. to about 375° C., and most preferably from about 225° C. to about 350° C.

Suitable carboxylated aminoethers for use in the step (ii) decarboxylation reaction can be prepared by the step (i) transesterification reaction or by other methods such as the carbonylation of 2-(N,N-dialkylamino)alkanols with carbon monoxide and oxygen at elevated temperatures in the presence of certain copper salts. Such a carbonylation process can be an alternative to the step (i) transesterification reaction and is encompassed within the generic scope of this invention. The carbonylation of certain alkanols with carbon monoxide and oxygen at elevated temperatures in the presence of certain copper salts to form dialkyl carbonates is disclosed in U.S. Pat. No. 4,360,477. It is also appreciated that two or more $CO_2$ synthons can be reacted under conditions effective to produce a carboxylated aminoether.

The step (ii) decarboxylation reaction can be conducted in the presence of an inert diluent which can be either a liquid or gas. When a liquid diluent is employed, it should preferably be a good solvent for the starting materials, inert under the reaction conditions, and of such a nature that separation from the aminoether product will not be difficult. For instance, the boiling points of the diluent and the aminoether product should differ by an adequate amount and there should be no tendency of the diluent to form an azeotrope with the desired aminoether product.

Examples of useful liquid diluents that meet the foregoing qualifications include benzene, toluene, xylene, ethylbenzene, anisole, heptane, octane, nonane, decane, dibutyl ether, and the like. Hydrocarbons are preferred.

Illustrative of gaseous diluents include, for example, nitrogen, methane, hydrogen, carbon monoxide or carbon dioxide. The gaseous diluent should of course be chosen so that it does not prevent the preparation of the desired aminoether products.

While the use of such diluents may be beneficial, the processes of this invention can be operated using pure starting material(s) as a liquid or gaseous feed. The degree of dilution of the starting material(s) with various diluents may vary considerably depending upon any process constraints restricting the use of the diluent. For example, in commercial production, the use of very large quantities of some gaseous diluents may be disadvantageous due to the cost of pumping large volumes of the gaseous diluent and increased difficulty in isolating the aminoether product, which increase the energy costs of the process. With liquid diluents, the use of very large quantities may be disadvantageous due to the energy cost associated with large recovery and recycle. If the processes of this invention are to be carried out using a gaseous diluent, in general it is recommended that the starting material(s) constitute from about 1 to about 95, and preferably about 5 to about 50, mole percent of the starting material/carrier feed. Increasing the dilution of the starting material with a gaseous diluent such as hydrogen may tend to increase the selectivity of the reaction to the particular products desired. The amount of liquid diluent can vary widely, for instance, from no diluent to about 90 weight percent or greater of the total weight of the starting materials.

For processes of this invention in which a carboxylated aminoether is contacted with a metal oxide catalyst under conditions effective to produce an aminoether or an active hydrogen-containing compound and a $CO_2$ synthon are contacted in the presence of a metal oxide catalyst under conditions effective to produce an aminoether or other related processes described herein, it is understood that the process conditions described herein for the step (ii) decarboxylation reaction can desirably be employed for such processes.

The processes of this invention are useful for preparing substituted and unsubstituted aminoethers such as those embraced by the formulae $ROR_4$ or $ROR_5$ wherein R, $R_4$ and $R_5$ are as defined above. It is understood that the R and $R_4$ substituents together and the R and $R_5$ substituents together can complete a heterocycloalkyl ring which can be substituted or unsubstituted. Preferred aminoethers include bis[2-(N,N-dialkylamino)alkyl]ethers characterized by the formula $R_1R_2NR_3OR_3NR_2R_1$ wherein $R_1$, $R_2$ and $R_3$ are as defined above. Other preferred aminoethers are characterized by the formulae $R_1R_2NR_3OR_4$ or $R_1R_2NR_3OR_5$ wherein $R_1$, $R_2$, $R_3$, $R_4$ and $R_5$ are as defined above. Illustrative aminoethers prepared by the processes of this invention include, for example, bis[2-(N,N-dimethylamino)ethyl]ether, bis[2-(N,N-dimethylamino)-1-methylethyl]ether, bis[3-(N,N-dimethylamino)propyl]ether, bis[2-(N,N-diethylamino)ethyl]ether, bis[2-(N,N-diethylamino-1-methylethyl]ether, bis[2-(N,N-diethylamino)propyl]ether, 2,2-dimorpholinodiethylether, (2-dimethylaminoethyl-3-dimethylaminopropyl)ether, 4-(2-methoxyethyl)morpholine, N-methylmorpholine, N-ethylmorpholine and the like. The preferred bis[2-(N,N-dialkylamino)alkyl]ether is bis[2-(N,N-dimethylamino)ethyl]ether. Illustrative of suitable bis[2-(N,N-dialkylamino)alkyl]ethers which can be prepared by the processes of this invention are described in U.S. Pat. Nos. 3,330,782, 3,400,157, 3,426,072, 3,480,675, 3,957,875, 4,177,212 and 4,247,482, the disclosures of which are incorporated herein by reference.

The aminoether products produced by the processes of this invention can be separated by distillation. For example, a crude reaction product can be subjected to a distillation-separation at atmospheric or reduced pressure through a packed distillation column. Reactive distillation may be useful in conducting the step (i) transesterification reaction.

The processes of this invention may be carried out using, for example, a fixed bed reactor, a fluid bed reactor, or a slurry reactor. The optimum size and shape of the catalyst will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low.

The processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the decarboxylation catalyst. When complete conversion is not desired or not obtainable, the starting materials can be separated from the aminoether product, for example by distillation, and the starting materials then recycled back into the reaction zone.

The processes are conducted for a period of time sufficient to produce the aminoethers. The exact reaction time employed is dependent, in part, upon factors such as temperature, nature and proportion of starting materials, and the like. The reaction time will normally be within the range of from about one-half to about 100 hours or more, and preferably from less than about one to about ten hours.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Illustrative of suitable reactants in effecting the processes of this invention include by way of example:
DMC—dimethyl carbonate
DEC—diethyl carbonate
UR—urea
PH—phosgene
BDEC—bis[2-(N,N-dimethylamino)ethyl]carbonate
DMAE—2-(N,N-dimethylamino)ethanol
DEAE—2-(N,N-diethylamino)ethanol
HEM—4-(2-hydroxyethyl)morpholine
BMEC—bis(2-N-morpholinoethyl)carbonate
DDC—(2-dimethylaminoethyl-3-dimethylaminopropyl)carbonate
HMMC—4-(2-hydroxyethyl)morpholine methyl carbonate
DMAP—1-(N,N-dimethylamino)-2-propanol
HEP—4-(2-hydroxyethyl)piperazine
DEG—diethylene glycol
DMEE—N,N-dimethylaminoethoxyethanol
BAE—bis(2-aminoethyl)ether
EDC—2-(N,N-dimethylamino)ethyl ethyl carbonate
DEDC—[2-(2'-dimethylaminoethoxy)ethyl]N,N-dimethyl carbamate
BDMEC—bis[2-(N,N-dimethylamino)-1-methylethyl]carbonate
BDPC—bis[2-(N,N-dimethylamino)propyl]carbonate
BDMPC—bis[3-(N,N-dimethylamino)propyl]carbonate
BDEEC—bis[2-(N,N-diethylamino)ethyl]carbonate
BDAEC—bis[2-(N,N-diethylamino)-1-methylethyl]carbonate
BDEPC—bis[2-(N,N-diethylamino)propyl]carbonate
MOR—morpholine
TMU—N,N,N',N'-tetramethyl urea Illustrative of suitable products prepared by the processes of this invention include by way of example:
BDEE—bis[2-(N,N-dimethylamino)ethyl]ether
DMDE—2,2-dimorpholinodiethylether
BDMEE—bis[2-(N,N-dimethylamino)-1-methylethyl]ether
BDPE—bis[3-(N,N-dimethylamino)propyl]ether
BDEEE—bis[2-(N,N-diethylamino)ethyl]ether
BDEPE—bis[2-(N,N-diethylamino)propyl]ether
DDE—(2-dimethylaminoethyl-3-dimethylaminopropyl)ether
MEM—4-(2-methoxyethyl)morpholine
NMM—N-methylmorpholine
NEM—N-ethylmorpholine Illustrative of permissible reactions encompassed within the scope of this invention include, for example, the following reactant/product combinations:

| REACTANT(S) | PRODUCT(S) |
| --- | --- |
| DEC, DE | BDEE |
| DMC, HM | DMDE |
| BDEC | BDEE |

-continued

| REACTANT(S) | PRODUCT(S) |
|---|---|
| BMEC | DMDE |
| HMMC | MEM |
| HM, DMC | MEM |
| DDC | DDE |
| DEG, TMU | BDEE |
| MOR, DMC | NMM |
| MOR, DEC | NEM |
| DMEE, TMU | BDEE |
| BAE, DMC | BDEE |
| EDC, DE | BDEE |
| UR, DE | BDEE |
| PH, DE | BDEE |

As used herein, the phrases "residue of an organic compound" and "residue of an organic compound containing nitrogen" are contemplated to include all permissible residues of organic compounds and organic compounds containing nitrogen. In a broad aspect, the permissible residues include acyclic and cyclic, branched and unbranched, carbocyclic and heterocyclic, aromatic and nonaromatic residues of organic compounds and organic compounds containing nitrogen. Illustrative organic compound residues include, for example, alkyl, aryl, cycloalkyl, heterocycloalkyl, alkyl(oxyalkylene, aryl(oxyalkylene), cycloalkyl(oxyalkylene), heterocycloalkyl(oxyalkylene), hydroxy(alkyleneoxy) and the like. The permissible residues can be substituted or unsubstituted and the same or different for appropriate organic compounds. This invention is not intended to be limited in any manner by the permissible residues of organic compounds and organic compounds containing nitrogen.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

Certain of the following examples are provided to further illustrate the processes of this invention.

EXAMPLE 1

Preparation of Decarboxylation Catalyst

A total of 79.4 grams (0.34 moles) of magnesium nitrate hexahydrate and 12.0 grams (0.032 moles) of aluminum nitrate nonahydrate were dissolved in 200 milliliters of deionized water to give a first solution. A total of 0.95 grams of sodium carbonate and 18 grams of sodium hydroxide were dissolved in 150 milliliters of deionized water to give a second solution. About 100 milliliters of distilled water was heated in a flask at a temperature of 40° C. and the first and second solutions were combined simultaneously with good agitation using a mechanical stirrer. The rates of addition of the first and second solutions were adjusted to maintain a pH of 9–10. The total addition took 3 minutes and a final pH of 9 was obtained. The contents were stirred at a temperature of 48° C. for a period of 30 minutes. The filter cake was washed with 300 milliliters of deionized water and dried at a temperature of 60° C. overnight to give a total of 20.1 grams of material. The dried filter cake was washed (ca. 200 milliliters three times) with deionized water at a temperature of 60° C. until the pH of the wash was neutral. The filter cake was then dried at a temperature of 80° C. overnight. The weight of the dried filter cake was 11.8 grams. The filter cake was then calcined in air at a temperature of 400° C. overnight to afford 7.3 grams of the catalyst having a magnesium/aluminum ratio of 10:1 and a surface area of 130 square meters per gram. This catalyst is referred to hereinafter as Catalyst A.

EXAMPLE 2

Preparation of Decarboxylation Catalyst

A total of 88.2 grams (0.34 moles) of magnesium nitrate hexahydrate and 132.0 grams (0.35 moles) of aluminum nitrate nonahydrate were dissolved in 400 milliliters of deionized water to give a first solution. A total of 10.6 grams of sodium carbonate and 60.8 grams of sodium hydroxide were dissolved in 400 milliliters of deionized water to give a second solution. About 100 milliliters of distilled water was heated in a flask at a temperature of 40° C. and the first and second solutions were combined simultaneously with good agitation using a mechanical stirrer. The rates of addition of the first and second solutions were adjusted to maintain a pH of 9–10. The total addition took 10 minutes. An additional 50 milliliters of 1 molar sodium hydroxide was added to obtain a final pH of 9. The contents were stirred at a temperature of 40° C. for a period of 30 minutes. The filter cake was dried at a temperature of 80° C. overnight to give a total of 94.7 grams of material. The dried filter cake was washed (ca. 300 milliliters three times) with deionized water at a temperature of 60° C. until the pH of the wash was neutral. The filter cake was then dried at a temperature of 80° C. overnight. The weight of the dried filter cake was 38.1 grams. The filter cake (12.0 grams) was then calcined in air at a temperature of 400° C. for a period of 3 hours to afford 1.6 grams of the catalyst having a magnesium/aluminum ratio of 1:1 and a surface area of 265 square meters per gram. This catalyst is referred to hereinafter as Catalyst B.

EXAMPLE 3

Preparation of Decarboxylation Catalyst

A total of 10 grams of filter cake prepared in Example 2 (prior to calcination at a temperature of 400° C.) was calcined in air at a temperature of 700° C. for a period of 3 hours to afford 5.9 grams of the catalyst having a magnesium/aluminum ratio of 1:1 and a surface area of 201 square meters per gram. This catalyst is referred to hereinafter as Catalyst C.

EXAMPLE 4

Preparation of Decarboxylation Catalyst

A total of 170.2 grams (0.66 moles) of magnesium nitrate hexahydrate and 12.6 grams (0.033 moles) of aluminum nitrate nonahydrate were dissolved in 400 milliliters of deionized water to give a first solution. A total of 1.02 grams of sodium carbonate and 32.0 grams of sodium hydroxide were dissolved in 400 milliliters of deionized water to give a second solution. About 100 milliliters of distilled water was heated in a flask at a temperature of 40° C. and the first and second solutions were combined simultaneously with good agitation using a mechanical stirrer. The rates of addition of the first and second solutions were adjusted to maintain a pH of 9-10. The total addition took 2 minutes and a final pH of 8.4 was obtained. The contents were stirred at a temperature of 40° C. for a period of 30 minutes. The filter cake was dried at a temperature of 80° C. overnight to give a total of the 64.8 grams of material. The dried filter cake was washed (ca. 300 milliliters three times) and deionized water at a temperature of 60° C. until the pH of the wash was neutral. The filter cake was then dried at a temperature of 80° C. overnight. The weight of the dried filter cake was 24.4 grams. The filter cake (8.5 grams) was then calcined in air at a temperature of 700° C. for a period of 3 hours to afford 5.0 grams of the catalyst having a magnesium/aluminum ratio of 20:1 and a surface area of 104 square meters per gram. This catalyst is referred to hereinafter as Catalyst D.

EXAMPLE 5

Preparation of Decarboxylation Catalyst

A total of 132.3 grams (0.51 moles) of magnesium nitrate hexahydrate and 66.0 grams (0.17 moles) of aluminum nitrate nonanhydrate were dissolved in 400 milliliters of deionized water to give a first solution. A total of 9.3 grams of sodium carbonate and 48.0 grams of sodium hydroxide were dissolved in 400 milliliters of deionized water to give a second solution. About 100 milliliters of distilled water was heated in a flask at a temperature of 40° C. and the first (350 milliliters) and second solutions were combined simultaneously with good agitation using a mechanical stirrer. The rates of addition of the first and second solutions were adjusted to maintain a pH of 8-9. The total addition took 8 minutes and a final pH of 8.5 was obtained. The contents were stirred at a temperature of 48° C. for a period of 15 minutes. The filter cake was dried at a temperature of 80° C. overnight to give a total of 86.0 grams of material. The dried filter cake was washed (ca. 300 milliliters three times) with deionized water at a temperature of 60° C. until the pH of the wash was neutral. The filter cake was then dried at a temperature of 80° C. overnight. The weight of the dried filter cake was 41.8 grams. The filter cake (12.0 grams) was then calcined in air at a temperature of 400° C. for a period of 3 hours to afford 7.3 grams of the catalyst having a magnesium/aluminum ratio of 3:1 and a surface area of 113 square meters per gram. This catalyst is referred to hereinafter as Catalyst E.

EXAMPLE 6

Preparation of Decarboxylation Catalyst

A total of 29.2 grams (0.11 moles) of magnesium nitrate hexahydrate and 87.0 grams (0.23 moles) of aluminum nitrate nonanhydrate were dissolved in 200 milliliters of deionized water to give a first solution. A total of 7.0 grams of sodium carbonate and 32.0 grams of sodium hydroxide were dissolved in 200 milliliters of deionized water to give a second solution. About 100 milliliters of distilled water was heated in a flask at a temperature of 40° C. and the first (180 milliliters) and second (180 milliliters) solutions were combined simultaneously with good agitation using a mechanical stirrer. The rates of addition of the first and second solutions were adjusted to maintain a pH of 8-9. The total addition took 12 minutes and a final pH of 8.2 was obtained. The contents were stirred at a temperature of 40° C. for a period of 20 minutes. The filter cake was dried at a temperature of 80° C. overnight to give a total of 39.1 grams of material. The dried filter cake was washed (ca. 300 milliliters three times) with deionized water at a temperature of 60° C. until the pH of the wash was neutral. The filter cake was then dried at a temperature of 80° C. overnight. The weight of the dried filter cake was 22.0 grams. The filter cake (12.0 grams) was then calcined in air at a temperature of 400° C. for a period of 3 hours to afford 7.8 grams of the catalyst having a magnesium/aluminum ratio of 1:2 and a surface area of 270 square meters per gram. This catalyst is referred to hereinafter as Catalyst F.

EXAMPLE 7

Preparation of Decarboxylation Catalyst

A total of 85.1 grams 0.33 moles) of magnesium nitrate hexahydrate and 6.3 grams (0.016 moles) of aluminum nitrate nonanhydrate were dissolved in 200 milliliters of deionized water to give a first solution. A total of 0.5 grams of sodium carbonate and 16.0 grams of sodium hydroxide were dissolved in 200 milliliters of deionized water to give a second solution. About 100 milliliters of distilled water was heated in a flask at a temperature of 40° C. and the first and second solutions were combined simultaneously with good agitation using a mechanical stirrer. The rates of addition of the first and second solutions were adjusted to maintain a pH of 8-9. The total addition took 8 minutes and a final pH of 8.8 was obtained. The contents were stirred at a temperature of 42° C. for a period of 15 minutes. The filter cake was dried at a temperature of 80° C. overnight to give a total of 24.4 grams of material. The dried filter cake was washed (ca. 300 milliliters three times) with deionized water at a temperature of 60° C. until the pH of the wash was neutral. The filter cake was then dried at a temperature of 80° C. overnight. The weight of the dried filter cake was 12.6 grams. The filter cake (12.4 grams) was then calcined in air at a temperature of 400° C. for a period of 3 hours to afford 8.0 grams of the catalyst having a magnesium/aluminum ratio of 20:1 and a surface area of 163 square meters per gram. This catalyst is referred to hereinafter as Catalyst G.

EXAMPLE 8

Preparation of Decarboxylation Catalyst

A total of 7.7 grams (0.03 moles) of magnesium nitrate hexahydrate and 118.53 grams (0.3 moles) of aluminum nitrate nonanhydrate were dissolved in 200 milliliters of deionized water to give a first solution. A total of 9.5 grams of sodium carbonate and 48.0 grams of sodium hydroxide were dissolved in 200 milliliters of deionized water to give a second solution. About 100 milliliters of distilled water was heated in a flask at a temperature of 40° C. and the first and second solutions were combined simultaneously with good agitation using a mechanical stirrer. The rates of addition of the first and second (175 milliliters) solutions were adjusted to maintain a pH of 8-9. The total addition took 8 minutes and a final pH of 11.1 was obtained. The contents were stirred at a temperature of 48° C. for a period of 15 minutes. The filter cake was dried at a temperature of 80° C. overnight to give a total of 58.3 grams of material. The dried filter cake was washed (ca. 300 milliliters three times) with deionized water at a temperature of 60° C. until the pH of the wash was neutral. The filter cake was then dried at a temperature of 80° C. overnight. The weight of the dried filter cake was 17.8 grams. The filter cake (12.0 grams) was then calcined in air at a temperature of 400° C. for a period of 3 hours to afford 9.2 grams of the catalyst having a magnesium/aluminum ratio of 1:10 and a surface area of 298 square meters per gram. This catalyst is referred to hereinafter as Catalyst H.

EXAMPLE 9

Preparation of Decarboxylation Catalyst

A total of 44.1 grams (0.17 moles) of magnesium nitrate hexahydrate and 66.0 grams (0.17 moles) of aluminum nitrate nonahydrate were dissolved in 200 milliliters of deionized water to give a first solution. A total of 4.8 grams of ammonium carbonate and 60 milliliters of ammonium hydroxide (28 weight percent) were dissolved in 200 milliliters of deionized water to give a second solution. About 100 milliliters of distilled water was heated in a flask at a temperature of 40° C. and the first and second solutions were combined simultaneously with good agitation using a mechanical stirrer. The rates of addition of the first and second solutions were adjusted to maintain a pH of 9–10. The total addition took 15 minutes and a final pH of 9.5 was obtained. The contents were stirred at a temperature of 41° C. for a period of 40 minutes. The filter cake was washed (ca. 300 milliliters three times) with deionized water at temperature of 60° C. until the pH of the wash was neutral. The filter cake was then dried at a temperature of 80° C. overnight. The weight of the dried filter cake was 30.5 grams. The filter cake was washed (ca. 300 milliliters three times) again with deionized water at a temperature of 60° C. and dried overnight at a temperature of 80° C. The weight of the dried filter cake was 21.6 grams. The filter cake (12.0 grams) was then calcined in air at a temperature of 400° C. for a period of 3 hours to afford 7.6 grams of the catalyst having a magnesium/aluminum ratio of 1:1 and a surface area of 223 square meters per gram. This catalyst is referred to hereinafter as Catalyst I.

EXAMPLE 10

Preparation of Decarboxylation Catalyst

A magnesium/aluminum material having a 2:1 magnesium/aluminum ratio was obtained from United Catalysts Inc., Louisville, Ky. This material was calcined in air at a temperature of 450° C. for a Period of 3 hours to afford the catalyst having a surface area of 192 square meters per gram. This catalyst is referred to hereinafter as Catalyst J.

EXAMPLE 11

Preparation of Decarboxylation Catalyst

A magnesium/aluminum material having a 1:1 magnesium/aluminum ratio was obtained from United Catalysts Inc., Louisville, Ky. This material was calcined in air at a temperature of 450° C. for a period of 3 hours to afford the catalyst having a surface area of 161 square meters per gram. This catalyst is referred to hereinafter as Catalyst K.

EXAMPLE 12

Preparation of Decarboxylation Catalyst

A total of 256.0 grams (1.0 moles) of magnesium nitrate hexahydrate and 125.0 grams (0.33 moles) of aluminum nitrate nonahydrate were dissolved in 700 milliliters of deionized water to give a first solution. A total of 100 grams of sodium carbonate and 140 grams of sodium hydroxide were dissolved in 1000 milliliters of deionized water to give a second solution. The first and second solutions were combined simultaneously with good agitation using a mechanical stirrer at or below a temperature of 35° C. over a period of 4 hours. The contents were then heated to a temperature of 65° C. and stirred overnight. The filter cake was washed (ca. 300 milliliters two to three times) with deionized water at a temperature of 60° C. until the sodium content of the resulting solid material was below 0.1 percent (dry basis). The solid material was then dried at a temperature of 125° C. under vacuum overnight. This material was calcined in air at a temperature of 400° C. for a period of 3 hours to afford the catalyst having a magnesium/aluminum ratio of 3:1 and a surface area of 164 square meters per gram. This catalyst is referred to hereinafter as Catalyst L.

EXAMPLE 13

Preparation of Decarboxylation Catalyst

A total of 5.0 grams 0.01 moles) of magnesium carbonate hydroxide pentahydrate and 10.0 grams (0.13 moles) of aluminum hydroxide hydrate were combined, 32 grams of deionized water was added to form a paste and the contents were then thoroughly mixed. The paste was calcined in air at a temperature of 400° C. for a period of 3 hours to afford 8.1 grams of the catalyst having a magnesium/aluminum ratio of 1:1. This catalyst is referred to hereinafter as Catalyst M.

EXAMPLE 14

Preparation of Bis[2-(N,N-dimethylamino)ethyl]carbonate

A total of 89.1 grams (1 mole) of 2-(N,N-dimethylamino)ethanol, 19.7 grams (0.167 moles) of diethyl carbonate and 1.0 gram of sodio 2-dimethylaminoethoxide (0.01 moles) were combined in a 250 milliliter round bottom flask equipped with a straight distillation head and magnetic stirrer. A vacuum was established and maintained at 50 mm Hg and the flask was heated to reflux. Initial reaction temperatures at reflux were 40° C. at the head and 48° C. on the kettle. Ethanol was removed over a period of 5.5 hours and trapped using a dry ice/acetone bath. After this time, a sample was removed from the kettle and analyzed by capillary gas chromatography. The kettle analyzed (area percent) for: 0.5 percent ethanol, 69.7 percent 2-(N,N-dimethylamino)ethanol, 0.1 percent diethyl carbonate, 0.1 percent bis[2-(N,N-dimethylamino)ethyl]ether, 1.5 percent 2-(N,N-dimethylamino)ethyl ethyl carbonate, and 28.1 percent bis[2-(N,N-dimethylamino)ethyl]carbonate. The reaction mixture was heated again for a period of 4.5 hours at reflux, after which time the head temperature rose to 56° C. and the kettle temperature rose to 60° C. A total of 15.6 grams of distillate was obtained. The distillate analyzed (area percent) by capillary gas chromatography for: 87.6 Percent ethanol, 0.6 percent ethyl carbonic acid, 3.7 percent 2-(N,N-dimethylamino)ethanol and 7.9 percent diethyl carbonate. After 9 hours at reflux, the 2-(N,N-dimethylamino)ethanol was removed overhead (56° C.–60° C. head temperature) slowly. After a period of 45 minutes, 58.2 grams of distillate was collected. The distillate analyzed (area percent) by capillary gas chromatography for 2-(N,N-dimethylamino)ethanol (98.8 percent) with minor amounts of ethanol and bis[2-(N,N-dimethylamino)ethyl]carbonate. The kettle (35.08 grams) analyzed (area percent) by capillary gas chromatography for bis[2-(N,N-dimethylamino)ethyl]carbonate (97.7 percent) with minor amounts of 2-(N,N-dimethylamino)ethanol, diethyl carbonate, 2-(N,N-dimethylamino)ethyl ethyl carbonate and bis[2-(N,N-dimethylamino)ethyl]ether. A total of 34.4 grams of the kettle material was charged to a 50 milliliter round bottom flask equipped with a distillation head and magnetic stirrer. The pressure was reduced to 8 mm Hg and the material was distilled overhead. The first fraction contained 4.6 grams of material. A second fraction containing 1.4 grams of material was obtained (maximum head temperature of 103° C. at 8 mm Hg) and a final fraction (head temperature of 108° C.–109° C. at 8 mm Hg) containing 25.2 grams of material was collected. A total of 2.2 grams was left as kettle residue. The last fraction analyzed (area percent) by capillary gas chromatography for bis[2-(N,N-dimethylamino)ethyl]carbonate (98.2 percent) with a minor amount of 2-(N,N-dimethylamino)ethanol (1.1 percent). A total material balance of greater than 99 percent was obtained and a theoretical yield of 73.8 percent (based on the final fraction of distillate) of bis[2-(N,N-dimethylamino)ethyl]carbonate was obtained.

EXAMPLES 15–27

Preparation of Bis[2-(N,N-dimethylamino)ethyl]ether

In the examples set forth in Table I below, an Applied Test Systems, Inc. Model 3620 Split Test Oven equipped with a preheater (stainless steel ⅛ inch o.d. ×2 feet) and ½ inch (o.d.) stainless steel reactor tube (8 inch length) was packed with catalyst and heated to the desired reaction temperature using a Honeywell Dial-A-Trol temperature controller. The temperatures at the top of the reactor and the bottom were monitored using a digital temperature readout. The liquid feed of neat bis[2-(N,N-dimethylamino)ethyl]carbonate was added (downflow) to the reactor via a Fluid Metering Inc. RP-G20 drive pump equipped with an ⅛ inch pump head. The system was maintained under nitrogen, which was introduced prior to the liquid preheater and was monitored with a rotometer. The product mixture was collected in a 100 milliliter round bottom flask, vented first to a dry ice/acetone trap and then a Firestone valve. Analysis was performed by capillary gas chromatography (FID) using a DB-1701 column. The process conditions and product analyses are set forth in Table I.

TABLE I

| Example No. | 15 | 16 | 17 | 18 | 19 |
|---|---|---|---|---|---|
| Process Parameters | | | | | |
| Catalyst Type | A | B | C | D | E |
| Catalyst Weight, gm. | 5.0 | 6.0 | 5.0 | 4.0 | 6.0 |
| Liquid Feed Rate, ml/min. | 0.30 | 0.33 | 0.33 | 0.37 | 0.33 |
| Gas Feed Rate, ml/min. | 37 | 37 | 37 | 37 | 37 |
| Temperature, °C. | 300 | 300 | 300 | 300 | 300 |
| Duration of Run, min. | 30 | 30 | 30 | 30 | 31 |
| Product Composition, area % | | | | | |
| 2-(N,N-dimethylamino)ethanol | 6.47 | 2.90 | 3.50 | 5.36 | 8.44 |
| N,N,N′,N′-tetramethylethylenediamine | 15.07 | 16.33 | 19.68 | 14.88 | 13.66 |
| Bis[2-(N,N-dimethylamino)ethyl]ether | 65.95 | 66.27 | 62.34 | 67.76 | 64.64 |
| Bis[2-(N,N-dimethylamino)ethyl]carbonate | 0.00 | 0.00 | 0.00 | 0.05 | 1.21 |
| Others | 12.51 | 14.50 | 14.48 | 11.95 | 12.05 |

| Example No. | 20 | 21 | 22 | 23 | 24 |
|---|---|---|---|---|---|
| Process Parameters | | | | | |
| Catalyst Type | F | G | H | I | J |
| Catalyst Weight, gm. | 4.5 | 6.0 | 6.0 | 6.0 | 6.0 |
| Liquid Feed Rate, ml/min. | 0.31 | 0.34 | 0.33 | 0.33 | 0.30 |
| Gas Feed Rate, ml/min. | 37 | 37 | 37 | 37 | 37 |
| Temperature, °C. | 300 | 300 | 300 | 300 | 30 |
| Duration of Run, min. | 32 | 32 | 30 | 30 | 30 |
| Product Composition, area % | | | | | |
| 2-(N,N-dimethylamino)ethanol | 5.28 | 8.59 | 9.52 | 2.81 | 5.28 |
| N,N,N′,N′-tetramethylethylenediamine | 14.07 | 15.61 | 14.07 | 13.84 | 16.98 |
| Bis[2-(N,N-dimethylamino)ethyl]ether | 66.17 | 63.38 | 53.97 | 72.11 | 64.99 |
| Bis[2-(N,N-dimethylamino)ethyl]carbonate | 0.00 | 0.00 | 0.31 | 0.00 | 0.00 |
| Others | 14.48 | 12.42 | 22.13 | 11.24 | 12.75 |

| Example No. | 25 | 26 | 27 |
|---|---|---|---|
| Process Parameters | | | |
| Catalyst Type | K | L | M |
| Catalyst Weight, gm. | 6.0 | 6.0 | 3.5 |
| Liquid Feed Rate, ml/min. | 0.33 | 0.33 | 0.27 |
| Gas Feed Rate, ml/min. | 37 | 37 | 37 |
| Temperature, °C. | 300 | 300 | 300 |
| Duration of Run, min. | 30 | 30 | 30 |
| Product Composition, area % | | | |
| 2-(N,N-dimethylamino)ethanol | 5.11 | 7.72 | 3.66 |
| N,N,N′,N′-tetramethylethylenediamine | 14.14 | 19.51 | 13.86 |
| Bis[2-(N,N-dimethylamino)ethyl]ether | 67.11 | 56.73 | 69.78 |
| Bis[2-(N,N-dimethylamino)ethyl]carbonate | 0.00 | 0.00 | 0.00 |
| Others | 13.64 | 16.05 | 12.70 |

EXAMPLE 28

Bis(2-N-morpholinoethyl)carbonate

A total of 28.8 grams (0.22 moles) of 4-(2-hydroxyethyl)morpholine, 9.0 grams (0.1 moles) of dimethyl carbonate and 0.38 grams of anhydrous potassium carbonate were combined in a 50 milliliter 3-neck round bottom flask equipped with a 12 inch vacuum-jacketed column packed with stainless steel screens and a distillation head. The contents were heated to reflux under nitrogen. An initial kettle temperature of 128° C. and a head temperature of 61° C. were observed. The contents were heated at reflux for a period of about 1.5 hours at which time the kettle temperature rose to 131° C. After this time, methanol (with some dimethyl carbonate) was slowly removed overhead for a period of about 50 minutes. Capillary gas chromatographic analysis showed about 50 percent of the desired product. The flask was then cooled to a temperature of 80° C. and an additional 3.0 grams of dimethyl carbonate was added. The contents were again heated to reflux for a period of about 30 minutes while removing methanol overhead to give a final kettle temperature of 200° C. A total of 4.3 grams of distillate was obtained. The kettle was filtered (vacuum) to remove the potassium carbonate. A total of 26.2 grams of this material was added to a 50 milliliter flask equipped with a 4 inch vacuum-jacketed column Packed with stainless steel screens and a distillation head. The flask was heated under vacuum (4 mm Hg) to remove the last traces of 4-(2-hydroxyethyl)morpholine (80° C. at 4mm Hg). The kettle fraction analyzed area percent by capillary gas chromatography as follows: 85.6 percent bis(2-N-morpholinoethyl)carbonate, 9.1 percent 2,2-dimorpholinodiethylether, and 2.1 percent 4-(2-hydroxyethyl)morpholine.

EXAMPLE 29

Preparation of 2,2-Dimorpholinodiethylether

Using the apparatus employed in Examples 15–27, a 20 percent (volume) solution of bis[2-N-morpholinoethyl)carbonate prepared in Example 28 in cyclohexane was passed through 6.0 grams of Catalyst J at a temperature of 300° C. and a liquid feed rate of 0.32 milliliters per minute. A total of 7.8 grams of product was recovered. Capillary gas chromatographic analysis (area percent) of this material showed 62.7 percent selectivity to 2,2-dimorpholinodiethylether at 97.5 percent bis(2-N-morpholinoethyl)carbonate conversion.

EXAMPLE 30

Preparation of 4-(2-Hydroxyethyl)morpholine methyl carbonate

A total of 13.1 grams (0.1 moles) of 4-(2-hydroxyethyl)morpholine, 27.0 grams (0.3 moles) of dimethyl carbonate and 0.4 grams of anhydrous potassium carbonate were combined in a 50 milliliter 3-neck round bottom flask equipped with a 4 inch vacuum-jacketed vigreaux column and a distillation head. The contents were heated to reflux under nitrogen, and after a period of 15 minutes (kettle temperature of 93° C. and a head temperature of 63° C.) methanol (with some dimethyl carbonate) was slowly removed overhead. After a period of about 2.5 hours, an additional 4.5 grams of dimethyl carbonate was added and the contents heated to reflux for another 1.5 hours. Capillary gas chromatographic analysis showed complete reaction of 4-(2-hydroxyethyl)morpholine. The flask was then cooled, filtered to remove potassium carbonate and charged to a clean 50 milliliter round bottom flask. The contents were distilled under vacuum (5 mm Hg) to give 9.14 grams (boiling point 117°–119° C. at 5 mm Hg) of 4-(2-hydroxyethyl)morpholine methyl carbonate (99 percent). The kettle residue (4.3 grams) analyzed (area percent) by capillary gas chromatography as follows: 4-(2-hydroxyethyl)morpholine methyl carbonate (32.8 percent) and bis(2-N-morpholinoethyl)carbonate (65.5 percent).

EXAMPLE 31

Preparation of 4-(2-Methoxyethyl)morpholine

Using the apparatus employed in Examples 15–27, a 20 percent (volume) solution of 4-(2-hydroxyethyl)morpholine methyl carbonate Prepared in Example 30 in cyclohexane was passed through 6.0 grams of Catalyst J at a temperature of 300° C. and a liquid feed rate of 0.27 milliliters per minute. A total of 7.4 grams of product was recovered. Capillary gas chromatographic analysis (area percent) of this material showed 67.7 percent selectivity to 4-(2-methoxyethyl)morpholine at 100 percent 4-(2-hydroxyethyl)morpholine methyl carbonate conversion.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

I claim:

1. A process for preparing aminoethers which comprises (i) contacting an active hydrogen-containing compound with a $CO_2$ synthon under conditions effective to produce a carboxylated aminoether, and (ii) contacting the carboxylated aminoether with a metal oxide catalyst under conditions effective to produce the aminoether, provided at least one of the active hydrogen-containing compound and $CO_2$ synthon contains nitrogen.

2. The process of claim 1 wherein the active hydrogen-containing compound comprises a substituted or unsubstituted alcohol, phenol, carboxylic acid, amine, thiophenol, mercaptan or amide.

3. The process of claim 1 wherein the active hydrogen-containing compound comprises a substituted or unsubstituted alkanolamine.

4. The process of claim 1 wherein the active hydrogen-containing compound comprises 2-(N,N-dimethylamino)ethanol, 1-(N,N-dimethylamino)-2-propanol, 2-(N,N-diethylamino)ethanol, 4-(2-hydroxyethyl)morpholine, morpholine, 4-(2-hydroxyethyl)piperazine, diethylene glycol, N,N-dimethylaminoethoxyethanol or bis(2-aminoethyl)ether.

5. The process of claim 1 wherein the H $CO_2$ synthon comprises a substituted or unsubstituted carbonate, chlorocarbonate, carbonic acid, carbamate, carbamic acid, oxalate, 2-oxazolidinone, urea, ester, phosgene, chloroformate, carbon dioxide, orthocarboxylate, sulfurous acid or sulfurous acid ester.

6. The process of claim 1 wherein the $CO_2$ synthon comprises dimethyl carbonate, diethyl carbonate, N,N,N',N'-tetramethyl urea, phosgene or urea.

7. The process of claim 1 wherein the carboxylated aminoether comprises a substituted or unsubstituted carboxyl-containing aminoether compound.

8. The process of claim 1 wherein the carboxylated aminoether comprises bis[2-(N,N-dimethylamino)ethyl]carbonate, bis[2-(N,N-diethylamino)ethyl]carbonate, bis(2-N-morpholinoethyl)carbonate, 2-(N,N-dimethylamino)ethyl ethyl carbonate, [2-(2'-dimethylaminoethoxy)ethyl] N,N-dimethyl carbamate, (2-dimethylaminoethyl-3-dimethylaminopropyl)carbonate or 4-(2-hydroxyethyl)morpholine methyl carbonate.

9. The process of claim 1 wherein the metal oxide catalyst comprises one or more Group IA metal oxides, Group IIA metal oxides, Group IIIB metal oxides, Group IVB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides or Group VIA metal oxides.

10. The process of claim 9 wherein the metal oxide catalyst comprises one or more oxides of magnesium, aluminum, calcium, strontium, gallium, beryllium, barium, scandium, yttrium, lanthanum, cerium, gadolinium, terbium, dysprosium, holmium, erbium, thulium, lutetium, ytterbium, niobium, tantalum, chromium, molybdenum, tungsten, titanium, zirconium, hafnium, vanadium, iron, cobalt, nickel, zinc, silver, cadmium, boron, indium, silicon, germanium, tin, lead, arsenic, antimony and bismuth.

11. The process of claim 1 wherein the metal oxide catalyst comprises at least one Group IIA metal oxide.

12. The process of claim 1 wherein the metal oxide catalyst comprises a Group IIA metal oxide and a Group IIIA metal oxide.

13. The process of claim 1 wherein the metal oxide catalyst comprises a Group IIA metal oxide and a Group IIIB metal oxide.

14. The process of claim 1 wherein the metal oxide catalyst comprises magnesium oxide and aluminum oxide.

15. The process of claim 1 wherein the metal oxide catalyst comprises mixed metal oxide.

16. The process of claim 1 wherein the aminoether comprises a substituted or unsubstituted aminoether.

17. The process of claim 1 wherein the aminoether comprises bis[2-(N,N-dimethylamino)ethyl]ether, 2,2-dimorpholinodiethylether, 4-(2-methoxyethyl)morpholine, (2-dimethylaminoethyl-3-dimethylaminopropyl)ether, N-methylmorpholine or N-ethylmorpholine.

18. A process for preparing bis[2-(N,N-dialkylamino)alkyl]ethers which comprises (i) contacting a 2-(N,N-dialkylamino)alkanol with a dialkyl carbonate under conditions effective to produce a bis[2-(N,N-dialkylamino)alkyl]carbonate, and (ii) contacting the bis[2-(N,N-dialkylamino)alkyl]carbonate with a metal oxide catalyst under conditions effective to produce the bis[2-(N,N-dialkylamino)alkyl]ether.

19. A process for preparing bis[2-(N,N-dimethylamino)ethyl]ether which comprises (i) contacting 2-(N,N-dimethylamino)ethanol with diethyl carbonate under conditions effective to produce bis[2-(N,N-dimethylamino)ethyl]carbonate, and (ii) contacting bis[2-(N,N-dimethylamino)ethyl]-carbonate with a magnesium:aluminum mixed metal oxide catalyst under conditions effective to produce bis[2-(N,N-dimethylamino)ethyl]ether.

20. A process for preparing aminoethers which comprises contacting an active hydrogen-containing compound with a $CO_2$ synthon in the presence of a metal oxide catalyst under conditions effective to produce the aminoether.

21. The process of claim 20 wherein the active hydrogen-containing compound comprises a substituted or unsubstituted alcohol, phenol, carboxylic acid, amine, thiophenol, mercaptan or amide.

22. The process of claim 20 wherein the active hydrogen-containing compound comprises a substituted or unsubstituted alkanolamine.

23. The process of claim 20 wherein the active hydrogen-containing compound comprises
2-(N,N-dimethylamino)ethanol,
1-(N,N-dimethylamino)-2-propanol,
2-(N,N-diethylamino)ethanol,
4-(2-hydroxyethyl)morpholine, morpholine,
4-(2-hydroxyethyl)piperazine, diethylene glycol,
N,N-dimethylaminoethoxyethanol or
bis(2-aminoethyl)ether 24. The process of claim 20 wherein the $CO_2$ synthon comprises a substituted or unsubstituted carbonate, chlorocarbonate, carbonic acid, carbamate, carbamic acid, oxalate, 2-oxazolidinone, urea, ester, phosgene, chloroformate, carbon dioxide, orthocarboxylate, sulfurous acid or sulfurous acid ester.

25. The process of claim 20 wherein the $CO_2$ synthon comprises dimethyl carbonate, diethyl carbonate, N,N,N',N'-tetramethyl urea, phosgene or urea.

26. The process of claim 20 wherein the carboxylated aminoether comprises a substituted or unsubstituted carboxyl-containing aminoether compound.

27. The process of claim 20 wherein the carboxylated aminoether comprises bis[2-(N,N-dimethylamino)ethyl]carbonate, bis[2-(N,N-diethylamino)ethyl]carbonate, bis(2-N-morpholinoethyl)carbonate, 2-(N,N-dimethylamino)ethyl ethyl carbonate, [2-(2'-dimethylaminoethoxy)ethyl]N,N-dimethyl carbamate, (2-dimethylaminoethyl-3-dimethylaminopropyl)carbonate or 4-(2-hydroxyethyl)morpholine methyl carbonate.

28. The process of claim 20 wherein the metal oxide catalyst comprises one or more Group IA metal oxides, Group IIA metal oxides, Group IIIB metal oxides, Group IVB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides or Group VIA metal oxides.

29. The process of claim 28 wherein the metal oxide catalyst comprises one or more oxides of magnesium, aluminum, calcium, strontium, gallium, beryllium, barium, scandium, yttrium, lanthanum, cerium, gadolinium, terbium, dysprosium, holmium, erbium, thulium, lutetium, ytterbium, niobium, tantalum, chromium, molybdenum, tungsten, titanium, zirconium, hafnium, vanadium, iron, cobalt, nickel, zinc, silver, cadmium, boron, indium, silicon, germanium, tin, lead, arsenic, antimony and bismuth.

30. The process of claim 20 wherein the metal oxide catalyst comprises at least one Group IIA metal oxide.

31. The process of claim 20 wherein the metal oxide catalyst comprises a Group IIA metal oxide and a Group IIIA metal oxide.

32. The process of claim 20 wherein the metal oxide catalyst comprises a Group IIA metal oxide and a Group IIIB metal oxide.

33. The process of claim 20 wherein the metal oxide catalyst comprises magnesium oxide and aluminum oxide.

34. The process of claim 20 wherein the metal oxide catalyst comprises mixed metal oxide.

35. The process of claim 20 wherein the aminoether comprises a substituted or unsubstituted aminoether.

36. The process of claim 20 wherein the aminoether comprises bis[2-(N,N-dimethylamino)ethyl]ether, 2,2-dimorpholinodiethylether, 4-(2-methoxyethyl)morpholine, (2-dimethylaminoethyl-3-dimethylaminopropyl)ether, N-methylmorpholine or N-ethylmorpholine.

37. A process for preparing bis[2-(N,N-dialkylamino)alkyl]ethers which comprises contacting a 2-[N,N-dialkylamino)alkanol with a dialkyl carbonate in the presence of a metal oxide catalyst under conditions effective to produce the bis[2-(N,N-dialkylamino)alkyl]ether 38. A process for preparing bis[2-(N,N-dimethylamino)ethyl]ether which comprises contacting 2-(N,N-dimethylamino)ethanol with diethyl carbonate in the presence of a magnesium:aluminum mixed metal oxide catalyst under conditions effective to produce bis[2-(N,N-dimethylamino)-ethyl]ether.

39. A process for preparing aminoethers which comprises contacting a carboxylated aminoether selected from the group consisting of bis[2-(N,N-dimethylamino)ethyl]carbonate, bis[2-(N,N-diethylamino)ethyl]carbonate, bis(2-N-morpholinoethyl)carbonate, [2-(2'-dimethylaminoethoxy)ethyl]N,N-dimethyl carbamate, (2-dimethylaminoethyl-3-dimethylaminopropyl)carbonate and 4-(2-hydroxyethyl)morpholine methyl carbonate, with a mixed metal oxide catalyst comprising a Group IIA metal oxide and a Group IIIA metal oxide, under decarboxylation conditions effective to produce the corresponding aminoether selected from the group consisting of bis[2-(N,N-dimethylamino)ethyl]ether, bis[2-(N,N-diethylamino)ethyl]ether, 2,2-dimorpholinodiethylether, (2-dimethylaminoethyl-3-dimethylaminopropyl)ether and 4-(2-methoxyethyl)morpholine.

40. A process for preparing bis[2-(N,N-dimethylamino)ethyl]ether which comprises contacting bis[2-(N,N-dimethylamino)ethyl]carbonate with a magnesium:aluminum mixed metal oxide catalyst under conditions effective to produce bis[2-(N,N-dimethylamino)ethyl]ether.

41. The process of claim 39 wherein the mixed metal oxide catalyst comprises magnesium oxide and aluminum oxide.

42. The process of claim 39 wherein the metal oxide catalyst has a surface area greater than about 50 m²/gm.

43. The process of claim 39 wherein the Group IIA metal oxide comprises from about 10 weight percent to about 90 weight percent of the weight of the catalyst.

44. The process of claim 39 wherein the mixed metal oxide catalyst is associated with a support material.

45. The process of claim 44 wherein the support comprises an alumina material or an alumina-silica material.

46. The process of claim 44 wherein the support comprises an silica material or a silica-alumina material.

47. The process of claim 44 wherein the support comprises from about 2 to about 50 percent by weight of the mixed metal oxide catalyst.

48. The process of claim 39 wherein the mixed metal oxide catalyst comprises:
(a) a material having the formula $$M_x^{2+}Q_y^{3+}(OH)_{2x+36-nz}A_z^{n-} \cdot a H_2O \quad (I)$$

wherein M is at least one divalent Group IIA metal cation; Q is at least one trivalent Group IIIA metal cation; and A is at least one anion providing a valence (n−), wherein n is 1 to 4 and wherein a is a positive number, M, Q and A are provided in a proportion such that x/y is a number equal to or greater than 1, z has a value greater than zero and 2x+3y−nz is a positive number, or
(b) a material prepared by calcining the material of formula (I) having the formula $$M_x^{2+}Q_y^{3+}(O)_{(2x+3y-nz)/2}D_z^{n-} \quad (II)$$

wherein M, Q, x, y, z and n have the same meanings defined above in connection with formula (I), and D is at least one nonvolatile anion.

49. The process of claim 48 wherein x/y is a number between 1 and 12 and z has a value which satisfies the relationship: x/z is between n and 12n.

50. The process of claim 48 wherein A is selected from the group consisting of carbonate, halide, phosphite, phosphate, chromate, sulfate, hydroxide, oxalate, acetate, nitrate, hexanoate, sebacate, vanadate, molybdate, tungstate and ferrocyanate.

51. The process of claim 48 wherein D is selected from the group consisting of halides, phosphite, phosphate, vanadate, molybdate, tungstate, sulfite, sulfate, chromate, arsenate, borate and chlorate.

52. The process of claim 48 wherein x/y is a number between 1 and 6 and z has a value which satisfies the relationship: x/z is between n and 6n.

53. The process of claim 48 wherein said material prepared by calcining the material of formula (I) has been heat treated at a temperature in the range of 200° C. to 800° C. for 12 to 24 hours.

54. The process of claim 48 wherein M is magnesium and Q is aluminum.

55. The process of claim 39 wherein said decarboxylation is carried out at a temperature from about 150° C. to about 500° C.

56. The process of claim 55 wherein said decarboxylation is carried out at a temperature from about 175° C. to about 375° C.

* * * * *